United States Patent
Shi et al.

(10) Patent No.: US 11,634,769 B2
(45) Date of Patent: Apr. 25, 2023

(54) METHOD OF DETERMINING TARGET NUCLEIC ACID

(71) Applicant: City University of Hong Kong, Kowloon (HK)

(72) Inventors: Peng Shi, Kowloon (HK); Zixun Wang, Kowloon (HK); Wenjun Zhang, Kowloon (HK); Linfeng Huang, Kowloon (HK); Xin Wang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/875,385

(22) Filed: Jan. 19, 2018

(65) Prior Publication Data

US 2019/0226024 A1    Jul. 25, 2019

(51) Int. Cl.
| | |
|---|---|
| *G01N 33/20* | (2019.01) |
| *C12Q 1/6876* | (2018.01) |
| *C12N 9/22* | (2006.01) |
| *C12Q 1/6811* | (2018.01) |
| *C12Q 1/686* | (2018.01) |
| *C12Q 1/6841* | (2018.01) |
| *C12Q 1/68* | (2018.01) |
| *C07H 21/04* | (2006.01) |
| *C07K 1/00* | (2006.01) |

(52) U.S. Cl.
CPC ............ *C12Q 1/6876* (2013.01); *C12N 9/22* (2013.01); *C12Q 1/686* (2013.01); *C12Q 1/6811* (2013.01); *C12Q 1/6841* (2013.01); *C12N 2310/122* (2013.01); *C12N 2310/141* (2013.01)

(58) Field of Classification Search
None
See application file for complete search history.

(56) References Cited

U.S. PATENT DOCUMENTS

| | | | | |
|---|---|---|---|---|
| 8,753,809 | B2* | 6/2014 | McReynolds | G01N 33/5308 435/325 |
| 9,394,547 | B2* | 7/2016 | Chen et al. | C12M 35/00 |
| 2007/0066521 | A1* | 3/2007 | Fauquet | A61K 38/162 435/375 |
| 2010/0209933 | A1* | 8/2010 | McReynolds et al. | G01N 33/5308 435/5 |
| 2013/0092541 | A1* | 4/2013 | Drndic | G01N 27/44791 204/543 |
| 2014/0045914 | A1* | 2/2014 | Ahn | C07K 14/08 530/350 |
| 2014/0295558 | A1* | 10/2014 | Chen | C12M 35/00 435/459 |

OTHER PUBLICATIONS

Sah et al., "Complete Genome Sequence of a 2019 Novel Coronavirus (SARS-CoV-2) Strain Isolated in Nepal", Microbiology Resource Announcements, vol. 9, Issue 11, Mar. 12, 2020, pp. 1-3. (Year: 2020).*
Forster et al., "A human gut bacterial genome and culture collection for improved metagenomic analyses", Nature Biotechnology, vol. 37, Feb. 2019, pp. 186-192. (Year: 2019).*
"COVID-19 Science Brief: Emerging SARS-CoV-2 Variants", Centers for Disease Control and Prevention, Jan. 28, 2021, pp. 1-4. (Year: 2021).*
"Transfer RNA", Wikipedia.com, accessed Sep. 23, 2021. (Year: 2021).*
Ying Wang et al; Poking cells for efficient vector-free intracellular delivery; Jul. 29, 2014; Nature Communications | 5:4466 DOI: 10.1038/ncomms5466.
Zixun Wang et al; Interrogation of Cellular Innate Immunity by Diamond-Nanoneedle-Assisted Intracellular Molecular Fishing; Nano Letters; Publication Date (Web): Sep. 11, 2015 | doi: 10.1021/acs.nanolett.5b03126.

\* cited by examiner

*Primary Examiner* — Bradley L. Sisson
(74) *Attorney, Agent, or Firm* — Renner Kenner Greive Bobak Taylor & Weber

(57) ABSTRACT

A method of determining one or more target nucleic acids in cells includes the steps of: delivering one or more probes into the cells, each of the one or more probes being capable of binding with corresponding target nucleic acid present in the cells to form a double-stranded sequence; inserting an array of functionalized nanoneedles into the cells to bind with the double-stranded sequence; and hybridizing the bound double-stranded sequence with a first and second DNA sequence to produce a hybridized product, the first and second DNA sequence being at least partially complementary to each other. A kit for determining a target nucleic acid in cells includes a first reagent comprising a probe for binding with the target nucleic acid to form a double-stranded sequence; and an array of functionalized nanoneedles comprising a protein for binding with the double-stranded sequence.

6 Claims, 22 Drawing Sheets
(6 of 22 Drawing Sheet(s) Filed in Color)

METHOD OF DETERMINING TARGET NUCLEIC ACID

TECHNICAL FIELD

The invention relates to an analytic method, in particular a method of determining a target nucleic acid in cells such as mammalian cells. The invention also concerns a kit for determining the target nucleic acid.

BACKGROUND OF THE INVENTION

MicroRNA (miRNA) is a class of non-coding small (18-23 nt) RNA which plays an important role in variety physiological and pathological activities. Gene expression or messenger RNA (mRNA) translation can be inhibited by targeting the specific mRNA, thereby regulating cellular translation. MiRNA is also known to be involved in cellular regulation such as immune response and pathogenesis. Accordingly, it can be a biomarker for diagnosis of diseases such as cancer or neural degenerative disease. However, miRNA is short in length and generally present in trace amount in the cells with frequent changes in expression.

Currently, qRT-PCR based miRNA kit is applied to determine the amount of miRNA. However, it utilizes complex steps for sample collection and testing and is rather time consuming. Another method—RNA sequencing (RNA-seq) has been recently developed for whole transcriptome profiling. It uses deep-sequencing technologies and provides a precise measurement of levels of transcripts and their isoforms. However, the high cost of platform building and maintenance limits its application area. Besides, RNA-seq also requires complicated steps to isolate RNAs.

Further developments have been made on in-situ miRNA analysis platform by combining nanotechnology. Current methods include introducing a nanoparticle or inserting a probe coated with nanoparticles to a cell for single-cell analysis. There are also methods for isolating miRNA from cell lysate for detection. However, these methods may cause irreversible damage to the cell and/or are not suitable for high-throughput analysis. Thus, they cannot achieve a real-time monitoring on the change of expression of the RNAs. Also, not all of these methods can be used to quantify the amount of miRNA in the cell.

Accordingly, there remains a need for an improved method for determining a target nucleic acid in a sample in particular living cells, which may be also suitable for high-throughput analysis.

SUMMARY OF THE INVENTION

In the first aspect, the invention provides a method of determining one or more target nucleic acids in cells, comprising steps of:
a) delivering one or more probes into the cells, each of the one or more probes being capable of binding with corresponding target nucleic acid present in the cells to form a double-stranded sequence;
b) inserting an array of functionalized nanoneedles into the cells to bind with the double-stranded sequence; and
c) hybridizing the bound double-stranded sequence with a first and second DNA sequence to produce a hybridized product, the first and second DNA sequence being at least partially complementary to each other.

In the second aspect, the invention pertains to a kit for determining a target nucleic acid in cells comprising:
i) a first reagent comprising a probe for binding with the target nucleic acid to form a double-stranded sequence; and
ii) an array of functionalized nanoneedles comprising a protein for binding with the double-stranded sequence.

In a preferred embodiment, the kit further comprises
iii) a second reagent comprising an initiating agent; and
iv) a third reagent comprising a first and second DNA sequence being at least partially complementary to each other, preferably the first and second DNA sequence has a stem-loop structure.

The invention provides a cost-effective and efficient approach for determining a target nucleic acid in cells while keeping the cells alive. The approach is also suitable for determining more than one target nucleic acid and therefore particularly useful in multiple sequences profiling. The inventors found that the invention is useful in multiple miRNA profiling which can specifically reveal the heterogeneity during mouse embryonic stem cell (mESC) differentiation. The application of the initiating agent and the hybridization steps allow amplification of signals for determination of the target nucleic acid which present at trace amount in the cells. Further, the method and kit directly obtain/extract the desired target nucleic acid without causing significant damages to the cells, and therefore it can minimize the loss of the target nucleic acid for determination.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3c is the image obtained when no probe was delivered to the cells, and no hybridization chain reaction has occurred. FIG. 3d is the image obtained after delivering the probe for binding with miR-34a sequence into the cells, and no hybridization chain reaction has occurred. FIG. 3e is the image obtained when no probe was delivered to the cells, with hybridization chain reaction. FIG. 3f is the image obtained after delivering the probe for binding with miR-34a sequence into the cells, with hybridization chain reaction to amplify the fluorescent signals.

FIGS. 9a and 9b show the results obtained from k-means cluster analyzes of the RNA data at Day 6 and Day 14, all the needle point is separated into 8 clusters. FIGS. 9c and 9d show the average images of cluster results at Day 6 and Day 14. Each square in FIGS. 9c and 9d represent the average mean intensity of one cluster and its channel.

DETAILED DESCRIPTION OF THE EMBODIMENTS

Figure 1A:
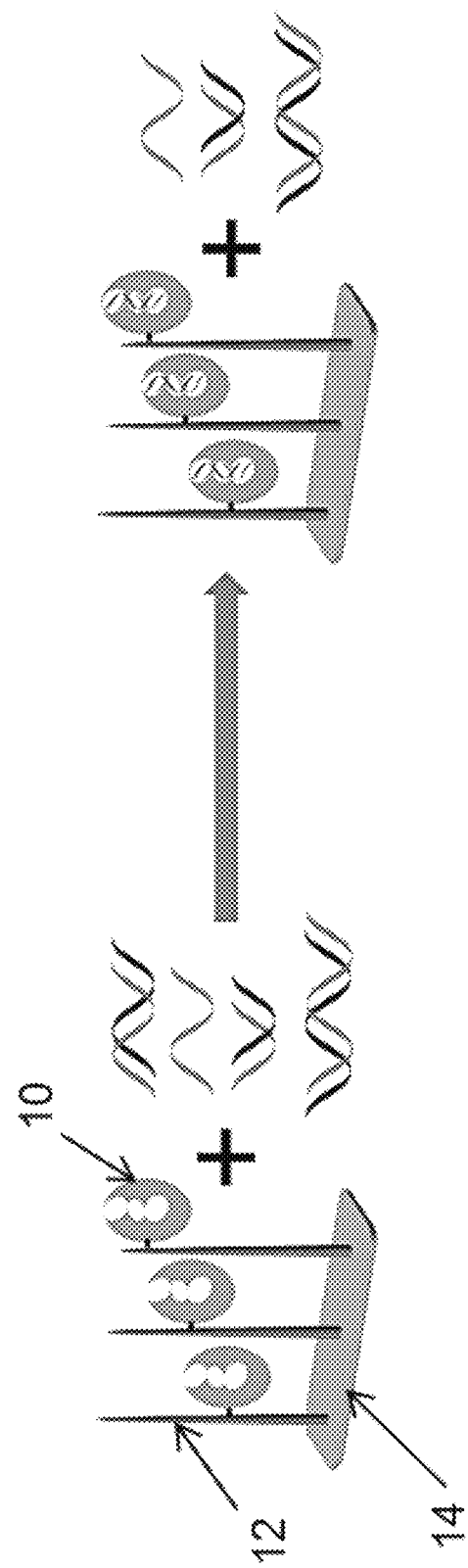
FIG. 1a is a schematic diagram showing the binding between the double-stranded sequence and protein carried by the functionalized nanoneedles in an embodiment of the present invention. The protein is capable of binding with a double-stranded sequence of a specific size and does not bind with single-stranded sequences.

The patent or application file contains at least one drawing executed in color. Copies of this patent or patent application publication with color drawing(s) will be provided by the Office upon request and payment of the necessary fee.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention in the first aspect provides a method of determining one or more target nucleic acids in cells, comprising steps of:

a) delivering one or more probes into the cells, each of the one or more probes being capable of binding with corresponding target nucleic acid present in the cells to form a double-stranded sequence;

b) inserting an array of functionalized nanoneedles into the cells to bind with the double-stranded sequence;

c) hybridizing the bound double-stranded sequence with a first and second DNA sequence to produce a hybridized product, the first and second DNA sequence being at least partially complementary to each other.

The term "target nucleic acid" refers to a sequence of nucleotides to be determined. The target nucleic acid may be a DNA sequence or a RNA sequence, naturally present, induced, or artificially induced in the cells. In an embodiment, the target nucleic acid is a single-stranded RNA sequence naturally present in the cells. The single-stranded RNA sequence may be a non-coding sequence selected from the group consisting of microRNA, siRNA, piRNA, snoRNA, snRNA, exRNA and scaRNA. In a specific embodiment, the target nucleic acid is microRNA (abbreviated as miRNA). The target nucleic acid may be composed of 15 to 30 nucleotides, 18 to 28 nucleotides, or preferably 18 to 23 nucleotides. The invention may also be applied to determine more than one target nucleic acid in the cells. In a further embodiment, the target nucleic acid may be a viral RNA produced by a virus.

As used herein, the term "probe" refers to a single-stranded sequence of nucleotides synthesized to match a specific region of target nucleic acid sequence, so as to allow a user to detect the presence or absence of the target nucleic acid, and/or the amount of it. The probe may be designed as a single-stranded DNA sequence or single-stranded RNA sequence, preferably a single-stranded RNA sequence, depending on the protein functionalized on the surface of nanoneedle. In an embodiment, the probe is a single-stranded RNA sequence for binding to a target RNA sequence. Preferably, the probe comprises a first region complementary to a specific region of the target nucleic acid, and a second region for binding to an initiating agent which is designed for initiating amplification. The second region may be composed of 5 to 20 base pairs (bp), i.e. have a length of between 5 to 20 bp, and at least partially complementary to the initiating agent. In particular, the second region has a length of between 5 to 15 bp, 5 to 10 bp, or 10 bp. The second region may be construed as an overhang sequence at an end of the probe and exposed to the environment. As such, when the initiating agent is added, it can bind with the overhang sequence readily to facilitate subsequent hybridization chain reaction. Different probe may have different second region so as to interact with different initiating agent. This approach allows detection of various target nucleic acids in the same sample of cells.

In a particular embodiment, the probe is devoid of fluorophore or chemiluminescent molecule.

Preferred probe binds its first region to the specific region of the corresponding target nucleic acid to form a double-stranded sequence. Said "double-stranded sequence" may be a double-stranded DNA sequence or a double-stranded RNA sequence, depends on the type of probe and target nucleic acid. In an embodiment, the double-stranded sequence formed is a double-stranded RNA sequence of about 15 to about 30 nucleotides, or about 18 to about 28 nucleotides, or about 19 to 25 nucleotides.

In the step a) of the invention, an array of non-functionalized nanoneedles may be used to deliver the probe into the cells. The step a) may comprise steps of:
  providing the cells in a medium containing the probe;
  placing the array of non-functionalized nanoneedles on the surface of the medium;
  applying a centrifugal force to move the array of non-functionalized nanoneedles towards the cells for piercing the cells, at about 200 to about 600 rpm for about 1 to about 6 minutes, or at about 300 rpm to about 500 rpm for about 2 to about 5 minutes, or at about 400 rpm for about 4 minutes;
  removing the array of non-functionalized nanoneedles from the cells by adding a fresh medium optionally containing the probe; and
  incubating the pierced cells for about 5 to 30 minutes, about 5 to 25 minutes, about 5 to 20 minutes, about 5 to 15 minutes, about 5 minutes or about 15 minutes, to allow the diffusion of the probe into the cells, and to form the double-stranded sequence.

After piercing, the probe diffuses into the cells via the temporary pierced holes on the cell membrane. In an alternative embodiment, the cells may be provided in a medium without the probe, and the probe is added with the fresh medium after piercing.

The term "an array of non-functionalized nanoneedles" refers an array of nanostructures which does not have any additional functional molecule on the surface of the nanostructure, and does not bind with any substance present in the cells. Additional functional molecule comprises a dye molecule such as fluorescent molecule, a metal molecule, a magnetic molecule, an aptamer or the like which react or bind with a target substance present in the cells. In the invention, the array of non-fictionalized nanoneedles may be used to create temporary holes on the cell membrane for intracellular delivery of the probe into the cells and thereby facilitating subsequent detection of target nucleic acid. Preferably, the non-functionalized nanoneedles may be prepared according to the method described in U.S. Ser. No. 14/719,416. The method as described in US/719,416 is incorporated herein. Preferred non-functionalized nanoneedles has a length of about 3 to about 8 μm, or about 4 to about 6 μm, or about 5 μm, and an average diameter of about 200 to 400 nm, or about 200 to 300 nm. The non-functionalized nanoneedles may be distributed on the array with a density of about $1 \times 10^6/cm^2$ to about $15 \times 10^6/cm^2$, or about $4 \times 10^6/cm^2$ to about $8 \times 10^6/cm^2$. In an embodiment, the array of non-functionalized nanoneedles may be provided in a form of patch having a size of about 1 $cm^2$, 2 $cm^2$, 3 $cm^2$, or the like.

In step b), an array of functionalized nanoneedles is used to bind with the double-stranded sequence formed in the cells. The term "functionalized nanoneedles" refers to nanoneedles which comprise a functional molecule on the surface of the nanoneedles for reacting and/or binding with, in particular binding with, a target substance present in the cells. Preferably, the functional molecule is a protein capable of binding with the double-stranded sequence formed in the step a). The protein is preferably a RNA binding protein for binding with a double-stranded RNA sequence. The RNA binding protein may be capable of binding with double-stranded RNA of about 15 to about 30 nucleotides, or about 18 to about 28 nucleotides, or about 19 to about 25 nucleotides. Preferred protein is a P19 protein capable of binding with double-stranded RNA of about 19 to about 25 nucleotides. With reference to FIG. 1a, the protein 10 is provided on the nanoneedles 12 of the array 14 to bind with the double-stranded sequence of appropriate size. The protein as used herein is advantageous in that it only captures small double-stranded sequence of certain size, and thus it provides an enhanced sensitivity and selectively towards the target nucleic acid. The protein does not bind with any single-stranded sequence or double-stranded sequence having a size larger or small than the required range. Therefore, only the desired double-stranded sequence can be attached on the functionalized nanoneedles. This approach also minimizes the interferences caused by pri-miRNA and pre-miRNA which have the same sequence of the target nucleic acid but present in hairpin form.

The array of functionalized nanoneedles may be prepared by using non-functional nanoneedles. In particular, an array of nanoneedles is subject to functionalization for adding a functional molecule capable of binding with the double-stranded sequence on the surface on the nanoneedles. As such, when the functionalized nanoneedles are inserted into the cells, the functional molecule can react and/or bind with the double-stranded sequence. The double-stranded sequence bound on the surface of the functionalized nanoneedles can be removed from the cells when the functionalized nanoneedles leave the cells. Preferably, the functionalized nanoneedles are prepared by firstly immersing the nanoneedles in an oxidizing solution to remove any organic impurities on the surface of the nanoneedles and introduce hydroxyl groups on the nanoneedles. Preferred oxidizing solution comprises piranha solution. The piranha solution may have about 75% to about 99% concentrated sulfuric acid and about 10% to about 40% hydrogen peroxide in a volume ratio of about 1:5 to 5:1. In an embodiment, the piranha solution has about 98% concentrated sulfuric acid and about 27.5% hydrogen peroxide in a volume ratio of 3:1. Secondly, the nanoneedles are cleaned by using a washing agent such as distilled water, alcohol, organic solvent or a combination thereof, and dried. Thirdly, the nanoneedles are respectively immersed into a biotin solution, a streptavidin-containing solution and a mixture containing the protein. In a particular embodiment, the nanoneedles are immersed in a sulfosuccinimidobiotin (NHS-biotin) solution for about 1 hour, and then immersed in a streptavidin solution for another 2 hours, lastly in a mixture containing P19 RNA binding protein for 1 hour. In between the steps, the nanoneedles are washed with a washing agent such as distilled water.

Those skilled in the art will appreciate other possible methods of providing the functional molecule on the surface of the nanoneedles to obtain an array of functionalized nanoneedles based on the disclosure provided herein, for the purpose of the invention.

In an alternative embodiment, the step a) may be carried out by using an array of functionalized nanoneedles to make holes on the cell membrane. In this embodiment, the step a) may comprise steps of:

providing the cells in a medium containing the probe;
placing an array of functionalized nanoneedles on the surface of the medium;
applying a centrifugal force to move the array of functionalized nanoneedles towards the cells for piercing the cells, at about 200 to about 600 rpm for about 1 to about 6 minutes, or at about 300 rpm to about 500 rpm for about 2 to about 5 minutes, or at about 400 rpm for about 4 minutes;
adding a fresh medium optionally containing the probe to lift up the array of functionalized nanoneedles from the cells; and
incubating the pierced cells for about 5 to 30 minutes, about 5 to 25 minutes, about 5 to 20 minutes, about 5 to 15 minutes, about 5 minutes or about 15 minutes, to allow the diffusion of the probe into the cells, and to form the double-stranded sequence.

The array of functionalized nanoneedles may then be used again for carrying out step b).

Preferably, the step b) is carried by centrifugation. After positioning the array of functionalized nanoneedles on the surface of the medium, a centrifugal force is applied to move the array of functionalized nanoneedles towards the cells. The centrifugation may be carried at about 200 to about 600 rpm for about 1 to about 6 minutes, or at about 300 rpm to about 500 rpm for about 2 to about 5 minutes, or at about 400 rpm for about 4 minutes. Then, the array of functionalized-nanoneedles is removed by adding a fresh medium to the cells. The functionalized nanoneedles are capable of binding with the double-stranded sequence formed in the step a) and extracting them out from the living cells via the temporarily formed holes. The bound double-stranded sequence remains on the functionalized nanoneedles after extraction. The application of the array of nanoneedles can extract the desired target substance from the cells without causing significant damages to the cells. In particular, the nanoneedles can readily bind with the double-stranded sequence present in the cytosol of the cell.

Figure 1B:
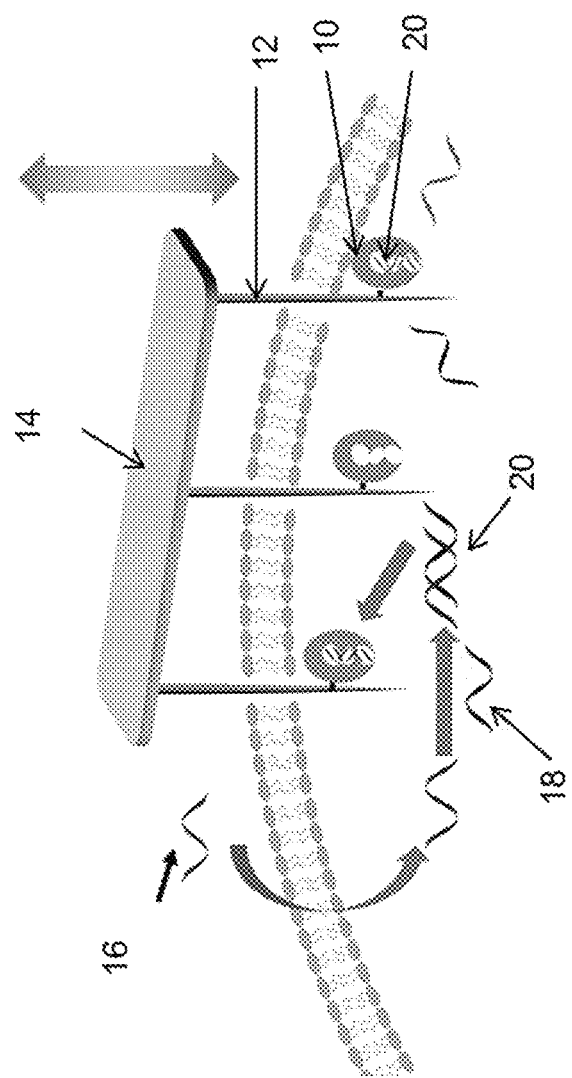
FIG. 1b is a schematic diagram showing the method of an embodiment of the invention. The RNA probes are delivered into the cell via pierced holes created by the functionalized nanoneedles, and bind with the target nucleic acid present in the cytosol of the cells to form a double-stranded RNA sequence. The double-stranded RNA sequence then binds with the protein on the functionalized nanoneedles.

With reference to FIGS. 1a and 1b, in an embodiment where a RNA probe 16 is used, it enters the cells via the pierced hole and binds with the target nucleic acid 18 to form a double-stranded RNA sequence 20. The double-stranded RNA sequence then binds with the protein 10 on the surface of the nanoneedles. After lifting up the array of functionalized nanoneedles 14, the double-stranded RNA sequence 20 bound on the nanoneedles will be removed from the cell. In another embodiment, two or more RNA probes with different sequences may be applied to bind with different target nucleic acids, thereby forming various double-stranded RNA sequences to be captured by the protein.

Prior to the step c), optionally, the functionalized nanoneedles bound with the double-stranded sequence are washed with a buffer solution such as sodium dodecyl sulfate, saline-sodium citrate, TWEEN™ solution or the like to remove impurities from the nanoneedles. Those skilled in the art would appreciate that other possible buffer solution may be applied to remove impurities without causing harm to the nucleic acid sequence.

Preferably, the step c) comprises:

immersing the functionalized nanoneedles into a first mixture containing an initiating agent, washing the functionalized nanoneedles; and
immersing the functionalized nanoneedles into a second mixture containing the first and second DNA sequence to produce the hybridized product.

The step c) further comprises a step of washing the functionalized nanoneedles for at least 5 minutes, at least 10 minutes, at least 15 minutes, or preferably about 15 to 30 minutes, after the immersion.

Figure 1C:
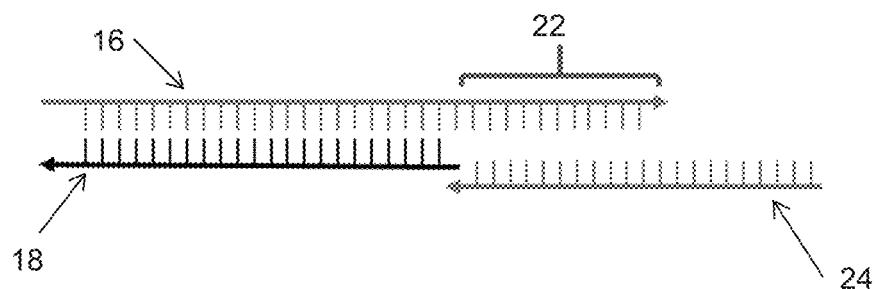
FIG. 1c is a schematic diagram showing an RNA probe of an embodiment of the invention. The RNA probe comprises an overhang sequence partially complementary to an initiating agent.

The term "initiating agent" as used herein refers to a short sequence of nucleotides which is capable of binding to a specific part of the probe and initiates hybridization chain reaction. Preferred initiating agent is a single-stranded sequence. As illustrated in FIG. 1c, the probe 16 preferably has a second region 22 for binding to the initiating agent 24, the second region may be called as an overhang sequence. When the initiating agent 24 binds with the double-stranded sequence in particular the second region 22 of the probe 16, it exposes a region for binding with the first or second DNA sequence added in the subsequent step. The initiating agent acts like a bridge having an end binding with the double-stranded sequence and another end for initiating hybridization. Preferably, the initiating agent comprises a single-stranded DNA sequence. It is particularly beneficial as single-stranded DNA is more stable than a single-stranded RNA and therefore facilitates efficient hybridization in particular for building long nucleotide sequence.

The first DNA sequence and second DNA sequence are provided to carry out hybridization and in particular to amplify the signal for determination of the target nucleic acid. The first DNA sequence and second DNA sequence are preferably synthesized based on the sequence of the initiating agent. Preferably, the first DNA sequence is partially complementary to the second DNA sequence and partially complementary to the initiating agent, and the second DNA sequence is partially complementary to the first DNA sequence and partially identical to the initiating agent. Accordingly, when the first DNA sequence binds with the initiating agent, it exposes the nucleotides complementary to the second DNA sequence. After the second DNA sequence binds with the first DNA sequence, the second DNA sequence exposes the part identical to the initiating agent for binding with another first DNA sequence. The reaction continues to extend the nucleotide sequence.

Figure 1D:
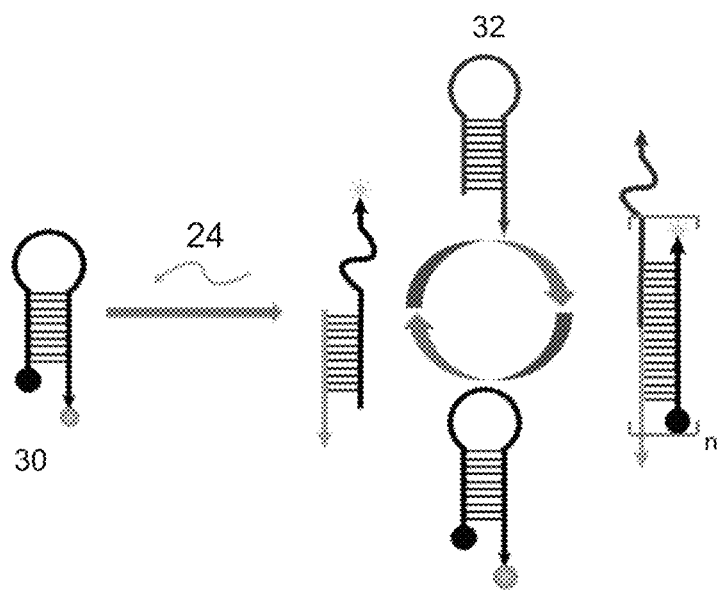
FIG. 1d is a schematic diagram showing the initiator, first and second DNA sequences applied in an embodiment of the invention. The first and second DNA sequences are provided in a stem-loop structure.
Figure 1E:
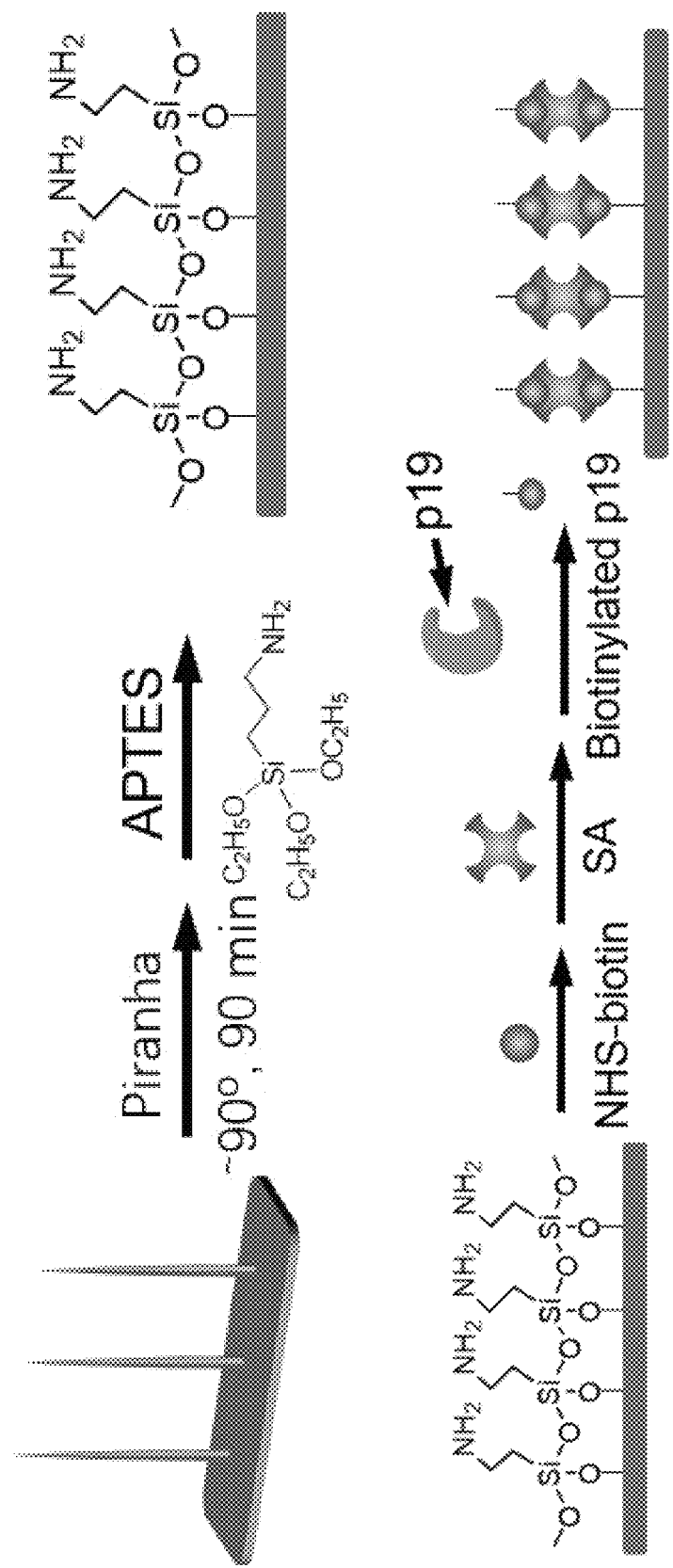
FIG. 1e is a schematic diagram showing the preparation of the functionalized nanoneedles used in an embodiment of the present invention.

In an embodiment, each of the first and second DNA sequence has a stem-loop structure, and the first and second DNA sequence hybridize with each other when one of them is open. The stem-loop structure (as hairpin-shaped) provides stability to the sequence. With reference to FIG. 1d, the first DNA sequence 30 opens to bind with the initiating agent 24 and exposes a part to hybridize with the second DNA sequence 32. Hybridization chain reaction between the first and second DNA sequences 30, 32 continues until quenching reaction takes place.

Preferably, at least one of the first and second DNA sequence comprises a fluorophore or chemiluminescent molecule, in particular a fluorophore. Fluorophore in general refers to a fluorescent chemical compound that can emit light upon light excitation. The incorporation of the fluorophore in the DNA sequences produces fluorescent signals for subsequent determination and quantification. The more the target nucleic acid being bound, the stronger the fluorescent signals produced. In another embodiment, both the first and second DNA sequences comprise a fluorophore. This is particular advantageous in that the method may be applied in detecting trace amount of the target nucleic acid in the cells. The inventors unexpectedly found that the method of the invention is capable of detecting a target nucleic acid in particular miRNA at a concentration as low as $10^{-16}$ M.

The washing step may be carried out in between steps to remove undesirable impurities such as excess imitating agent attached on the functionalized nanoneedles to minimize interference caused by the impurities. Those skilled in the art are capable of selecting suitable washing buffer to wash the functionalized nanoneedles. The person having the skills will also appreciate suitable concentration of the initiating agent, the first and second DNA sequences applied in the method of the invention.

After the step of immersing the functionalized nanoneedles into a second mixture containing the first and second DNA sequence, the functionalized nanoneedles are incubated in the second mixture for a period of time to allow hybridization to occur and produce the hybridized product on the functionalized nanoneedles. Preferably, the incubation may last for about 5 minutes to 24 hours, about 5 minutes to 12 hours, about 5 minutes to 8 hours, about 5 minutes to 4 hours, or about 1 hour to 4 hours. After incubation, the functionalized nanoneedles are washed with a washing buffer for about 30 minutes to remove impurities or residues attached on the nanoneedles.

The step c) comprises determining the presence or absence and the amount of the target nucleic acid. In an embodiment where the first DNA sequence comprises a fluorophore, the presence or absence and the amount of the target nucleic acid is determined with a fluorescence microscope. For instance, the array of functionalized nanoneedles is observed under a confocal microscope in particular a confocal laser scanning microscope at appropriate wavelength depending on the fluorophore used. The fluorescent signal produced is transferred into gray value for quantification. The person having the skills in the art will appreciate other suitable methods for measuring the fluorescent signals.

Figure 7:
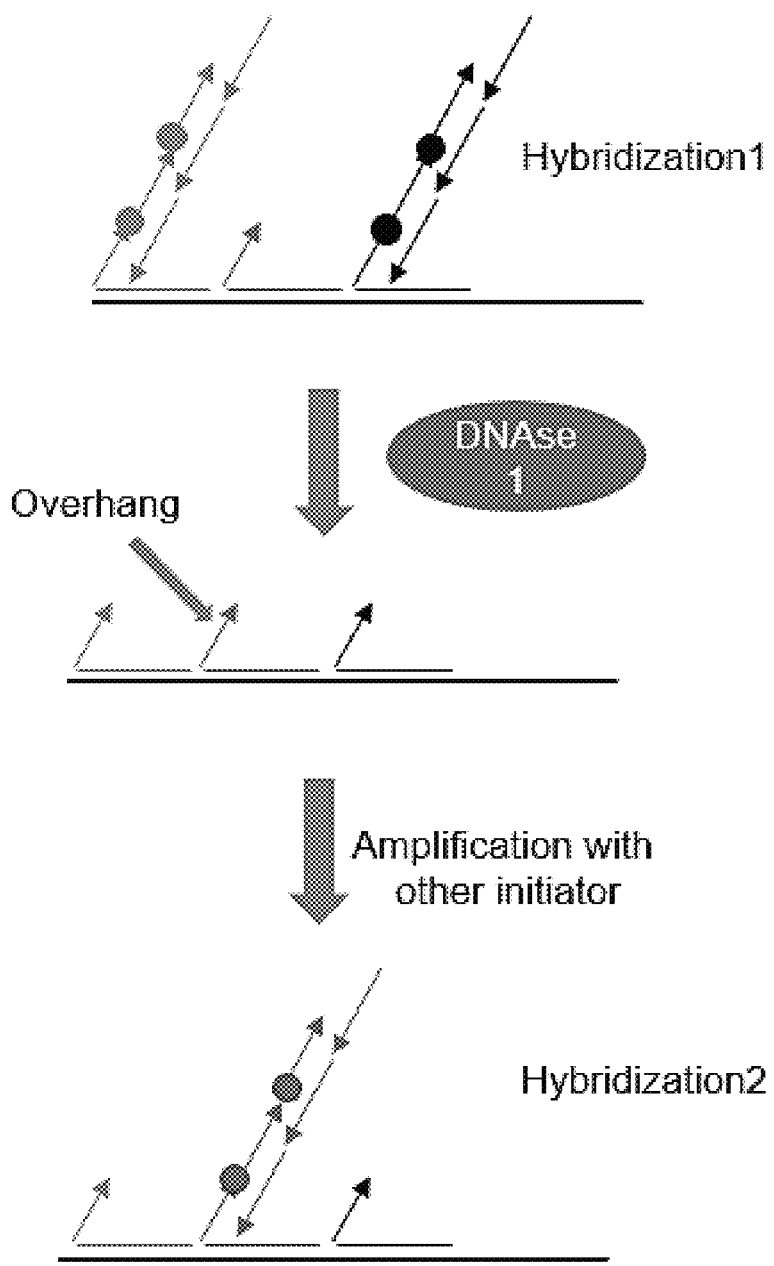
FIG. 7 is a schematic diagram showing the process of removing the first hybridized product from the functionalized nanoneedles before conducting another hybridization chain reaction (amplification) with another set of initiating agent and DNA sequences so as to determine another target nucleic acid.

It would be appreciated that the present invention is exceptionally suitable for determining more than one target nucleic acid in the cells, in particular living cells. In an embodiment where the method is applied to determine at least two target nucleic acids, at least two probes may be applied to bind with each of corresponding target nucleic acid. Preferably, at least two initiating agents are used to bind with corresponding double-stranded sequence formed and further DNA sequences are applied for hybridization. In a specific embodiment where two or more target nucleic acids are to be determined, the step c) further includes a step of adding a DNase after determination of each target nucleic acid. The addition of DNase can remove the hybridized product prepared from the first and second DNA sequence which reflects the presence or absence and the amount of the first target nucleic acid. Subsequently, the second initiating agent and DNA sequences for the second initiating agent may be added to determine the second target nucleic acid. The invention as described allows multiple determination of various target nucleic acid on the same array of the nanoneedles. It saves resources and time on determination. FIG. 7 demonstrates how DNase may be applied.

The method as described herein has high specificity and sensitivity towards miRNA detection in living cells. The application of nanoneedle array provides an effective method for delivering probe into the cells and extracting the target substance from the cells for determination and quantification. In particular, the expression of RNA sequences such as miRNA present in the cytosol of the cells can be readily measured. The method also minimizes the damages caused to the cells. There is no need to carry out cell lysis to disrupt the entire cell for extracting the target nucleic acid from the cells and is therefore particularly useful for high-throughput screening or measurement. Further, as the cells are kept alive during operation, it allows a user to monitor the cellular change of the cells over a period of time. For instance, the method may be conducted repeatedly once per day/2 days. I.e. it may be applied in real-time monitoring of cellular RNA variation.

The inventors also found that when the cells are exposed under some extrinsic genotoxic stresses, UV and cis-platin, there is a remarkable variation of the miRNA expression level in a short period of time. Accordingly, the method is suitable for investigating the early stage RNA variation in particular miRNA variation, in response such as cellular innate immune response. The application of amplification of the fluorescent signals further saves time and avoids complicated procedures for detection. In case where a higher resolution microscopy is used, more target nucleic acids can be determined.

Turning to the second aspect, the invention provides a kit for determining a target nucleic acid in cells in particular living cells. The kit comprises:
  i) a first reagent comprising a probe as described above for binding with the target nucleic acid to form a double-stranded sequence; and
  ii) an array of functionalized nanoneedles comprising a protein for binding with the double-stranded sequence.

The kit is suitable for use in the method as described above.

The probe is as described above and refers to a single-stranded sequence of nucleotides synthesized to match a specific region of target nucleic acid sequence. Preferred probe comprises a first region complementary to the target nucleic acid, and a second region for binding to an initiating agent. For instance, the second region of the probe has a length of between 5 bp to 20 bp. The array of functionalized nanoneedles is as described above and comprises a functional molecule for binding with double-stranded sequence. Preferably the functionalized nanoneedles are made of diamond and the functional molecule is preferably a protein. In an embodiment, the protein is RNA binding protein capable of binding with a double-stranded RNA sequence in particular binding with double-stranded RNA of about 15 to about 30 nucleotides, or about 18 to about 28 nucleotides, or about 19 to about 25 nucleotides. Preferred RNA binding protein is a p19 protein capable of binding with double-stranded RNA of about 19 to about 25 nucleotides. This functional molecule is suitable for determining short RNA sequences in the cytosol of the cells.

In an embodiment where the target nucleic acid is a single-stranded RNA sequence, double-stranded RNA sequence is formed by binding the probe with the target nucleic acid.

The kit may further comprise an array of non-functionalized nanoneedles. The array of non-functionalized nanoneedles is as described above and may be applied to pierce the cells under centrifugation for intracellular delivery of the probe. Preferably, the non-functionalized nanoneedles are diamond nanoneedles which are chemically inert and do not have any additional functional molecules attached thereon for binding with any substance in the cells. The non-functionalized nanoneedles may have the properties described above. In particular, the array of non-functionalized nanoneedles and the array of functionalized nanoneedles are provided is a form of patch having a size of about 1 cm$^2$, 2 cm$^2$, 3 cm$^2$, or the like. The kit may comprise more than one array of functionalized nanoneedles and more than one array of non-functionalized nanoneedles.

In another embodiment, the kit further comprises
iii) a second reagent comprising an initiating agent as described above which is partially complementary to the second region of the probe; and
iv) a third reagent comprising a first and second DNA sequence being at least partially complementary to each other. In particular, the first DNA sequence is partially complementary to the initiating agent, and the second DNA sequence has a part identical to the initiating agent.

Preferably, at least one of the first and second DNA sequence comprises a fluorophore which can be measured under fluorescent microscope. Each of the first and second DNA sequence has a stem-loop structure, and the first and second DNA sequence hybridize with each other when one of them is open.

The method and the kit of the present invention allows for a highly advantageous approach for determining the presence and/or amount of target nucleic acid in particular a RNA sequence in a sample of living cells. The inventors found that the method and the kit can determine the target nucleic acid at a concentration as low as $10^{-16}$M. The method is also easy to operate and saves operation time.

Accordingly, the present invention provides an improved approach for studying cellular response in particular variation in the cellular level. The method and kit are also suitable for diagnosis of diseases, and for determination of health conditions or pathological conditions of a subject. For instance, it may be used to determine the expression of target viral nucleic acid or biomarker for a disease. It would be also appreciated that the method and kit as disclosed herein are also useful in laboratory research and other clinical studies.

EXAMPLES

Example 1

Cell Culture

HB9::GFP mESCs were acquired from the Stem Cell Core Facility of Columbia University. ESCs were seeded in a Petri-dish coated with 0.1% gelatin and were further cultured in an incubator at 37° C. with 5% CO2 for proliferation. After three days, ESCs were trypsinized for cell seeding. 250 mL of ESC culture medium consisted of 200 mL of EmbryoMax DMEM (SLM-220-B, Chemicon/Millipore), 37.5 mL of fetal bovine serum (FBS) (SH30070.03, GE), 2.5 mL of EmbryoMax MEM Non-essential Amino Acids (TMS-001-C, Chemicon/Millipore), 2.5 mL of Nucleosides (ES-008-D, Chemicon/Millipore), 2.5 mL of 200 mM L-Glutamine (25030-081, Invitrogen), 2.5 mL of Pen/Strep (10,000 units/mL Penicillin; 10,000 μg/mL Streptomycin), 180 μL of diluted 2-mercaptoethanol (diluted 1/100 in PBS-with Mg & Ca, M-7522, Sigma) and 25 μL of LIF/ESGRO (ESG1107, Chemicon/Millipore) was prepared. Afterwards, the ES medium was replaced by a differentiation medium. 450 mL of differentiation medium consisted of 200 mL of Advanced DMEM/F12 (12634-010, Invitrogen), 200 mL of Neurobasal Medium (21103-049, Invitrogen), 46 mL of Knockout-SR (10828-028, Invitrogen), 4.6 mL of Pen/Strep, 4.6 mL of L-Glutamine, 320 μL of diluted 2-mercaptoethanol, 450 μL of retinoic acid/DMSO solution (Sigma-Aldrich, USA) and 450 μL of smoothened agonist/DMSO solution (Sigma-Aldrich, USA) was used. After culturing the cells in the differentiation medium for 2 days, a mixture of retinoic acid (RA) and smoothened agonist (SAG) were added into the medium for inducing motor neuron differentiation. The differentiation medium was further supplemented with 4.5 μL of glial derived neurotrophic factor (GDNF), 9 mL of B27 (Invitrogen, USA) and 4.5 mL of N2 supplement (Invitrogen, USA) after 3 days of in vitro differentiation.

Example 2

Nanoneedle Fabrication and Characterization

The fabrication of the nanoneedles in particular non-functionalized nanoneedles includes two processes. Deposition of nanodiamond film and subsequent bias-assisted reactive ion etching (RIE) by electron cyclotron resonance microwave plasma chemical vapor deposition (ECR-MPCVD). N-type (001) silicon wafers of 3 in. in diameter were used as substrate. Before nanodiamond deposition, the substrate was ultrasonically abraded for 60 min in a suspension of nanodiamond powders with a grain size of 5 nm in ethanol. Nanodiamond films of 7 μm thick were deposited in step one using a commercial ASTeX MPCVD equipped with a 1.5 kW microwave generator. The nanodiamond deposition was performed in the plasma induced in a 10% $CH_4/H_2$ mixture at a total pressure of 30 Torr and total gas flow rate of 200 sccm. The microwave power and deposition temperature were maintained at 1200 W and 800° C., respectively. After the nanodiamond film deposition was finished, the second step of RIE was performed using electron cyclotron resonance MPCVD. The ASTeX microwave source employed a magnetic field of 875 G generated by an external magnetic coil. The RIE conditions were as follows: a mixture of 45% Ar and 55% $H_2$ was used as the reactive gases at a total flow rate of 20 sccm; the substrate bias was −200 V; the reactant pressure was $7\times10^{-3}$ Torr. The etching duration was 3 h and the input microwave power was 800 W, respectively. The morphology of diamond-nanoneedle patch was characterized by a Philips FEG SEM XL30. The sample was tilted 90° for SEM.

Example 3

Functionalization of Nanoneedles

An array of non-functionalized nanoneedles prepared according to Example 2 was subject to functionalization to form an array of functionalized nanoneedles. Diamond-nanoneedles as prepared were first bathed in a piranha solution (3:1, v/v, 98% $H_2SO_4$: 27.5% $H_2O_2$) at 90° C. for 1.5 h and then cleaned by distilled water, methanol, a mixture of methanol/dichloride methane (DCM) (3:1, v/v), and DCM sequentially. The nanoneedle patch was dried with nitrogen and then immersed in APTES solution (20% in DCM) overnight in nitrogen protected environment. Ethanol, 2-propanol, and distilled water were used to wash the nanoneedle patch step by step, which was followed by nitrogen drying. After cleaning, the nanoneedle patch was sequentially immersed in a NHS-Biotin solution (purchased from Sigma-Aldrich) (1 µg/mL in PBS) for 1 h, a streptavidin solution containing streptavidin/alex-488 modified streptavidin (purchased from Sigma-Aldrich) (10 µg/mL in PBS) for 2 h, and a solution containing biotin—biotinylated p19 siRNA binding protein (NEB) solution (1 µg/mL in PBS) for 1 h. The patch was rinsed with distilled water between different steps. Finally, a patch of functionalized nanoneedles carrying p19 protein was obtained.

Example 4

Intracellular Delivery of the Probe and Extraction of the Target Nucleic Acid

Intracellular delivery of a RNA probe was performed using a centrifugation controlled process. For suspension cells, the culture medium was first removed, and the cells were mixed with 100 µL of a solution containing the RNA probe at 10 nM in concentration. In case where various target nucleic acids are to be determined, various probes may be used and each probe is applied at a concentration of 10 nM. It would be appreciated that the RNA probe may be provided at a concentration of between 1 nM to 10 nM depends on the conditions. Nanoneedle patch was placed facing toward cells. The whole setup was then placed in a centrifuge with a plate-rotor and spun at 400 rpm (22.8 g) for 4 min. After first centrifugation, the setup was stopped and incubated for more than 5 min allowing the probe to diffuse into the cells and forming dsRNA with the target nucleic acid. Then, the cells were pierced again with the functionalized nanoneedles carrying p19 protein to extract the dsRNA.

Example 5

Hybridization Chain Reaction

Each RNA probe has a 10 bp overhang sequence which can be used to amplify the signal in a fluorescent enabled hybridization chain reaction way. After fishing dsRNA, needle patch was washed with 0.05% SDS, after that, the patch was immersed in a single strand DNA solution (5 nM (the concentration also can be varied from 5 nM-10 nM) in 5×SSC and 0.05% TWEEN™), this step we called initiator binding. After binding with initiator, the needle patch was washed with wash buffer (0.5x ssc and 0.01% TWEEN™) for 5 min and then hybridize with hairpin DNA1 and DNA2 (20 nM in 5×SSC and 0.05% TWEEN™) to acquire an enhanced fluorescent signal. After thorough rinsing with wash buffer for 30 min, confocal microscopy was used to image and quantify the amount of miRNA bonded on the surface of diamond-nanoneedles.

Example 6

Determining the Detection Limitation of the Method

Figure 2:
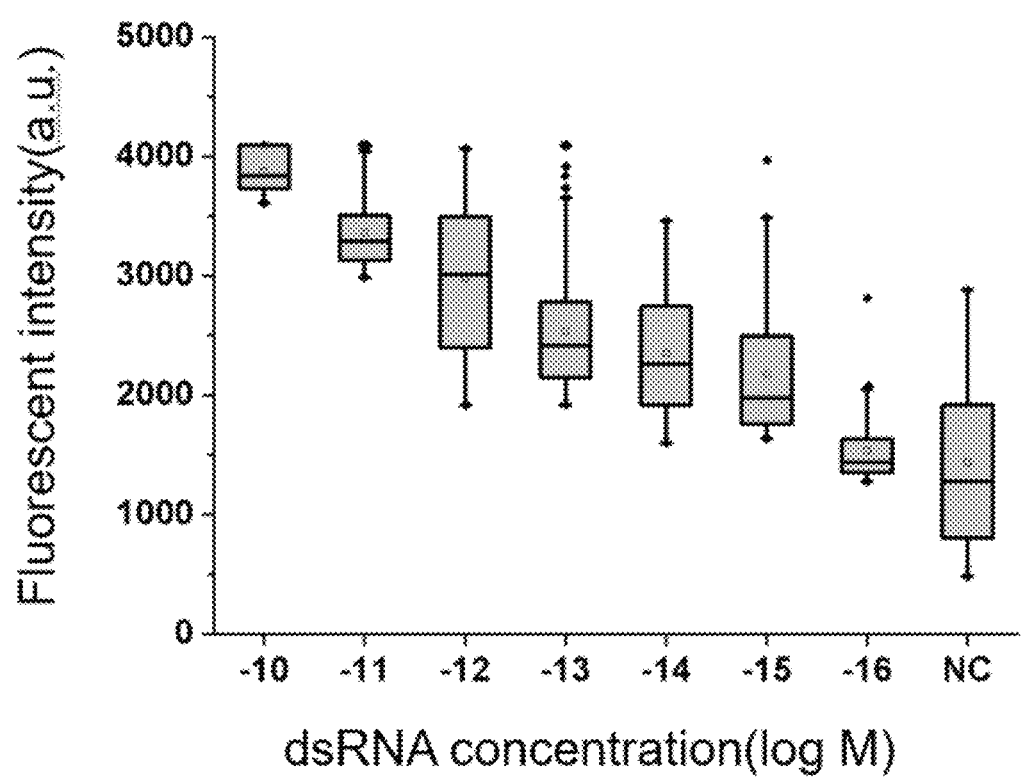
FIG. 2 shows the fluorescent intensity measured by binding the double-stranded RNA with the functionalized nanoneedles at different concentration of a dsRNA in DMEM medium.

MiRNAs are generally expressed at a relative low level in cytoplasm. The inventors first tested the detection sensitivity of the method of the invention. The inventors immersed arrays of functionalized nanoneedles into a series of DMEM medium with different concentration of double-stranded RNA. The arrays were incubated in the respective media for 15 minutes so as to allow the double-stranded RNA to bind with the p19 protein on the nanoneedles. After the incubation, the arrays were washed with a washing buffer, and subject to a solution containing an initiating agent. The initiating agent is useful in initiating a hybridization chain reaction as well as signal amplification (FIG. 1d). The hybridization involved a first and second DNA sequence to label the double-stranded RNA with a fluorophore and amplify the signal produced by the fluorophore. Lastly, a laser scanning confocal microscopy (Leica SP8) was applied to transfer the fluorescent signal into gray value as an image for further quantification. With reference to FIG. 2, the method is capable of determining miRNA at a concentration as low as $10^{-16}$ M.

Example 7

Determination of miR-34a Present in the Living Cells

Figure 3A:
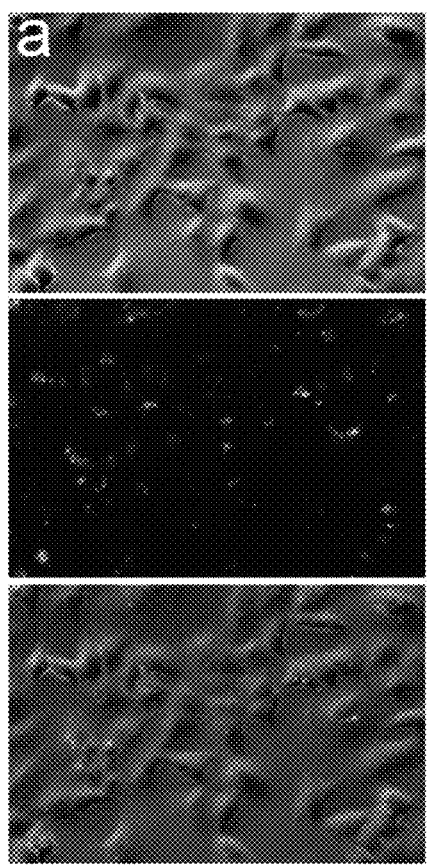
FIG. 3a shows the microscopic images of A549 cells after extracting RNA sequence of let-7a from the cells, in which the upper panel is a phase contrast image of the cells, the middle panel is the fluorescent image of the cells which were dyed with 1,1'-bis(3-hydroxypropyl)-3,3,3',3'-tetramethylindocarbocyanine dye, after RNA probe delivery and RNA extraction, and the lower panel is a merged image of the upper and middle ones.
Figure 3B:
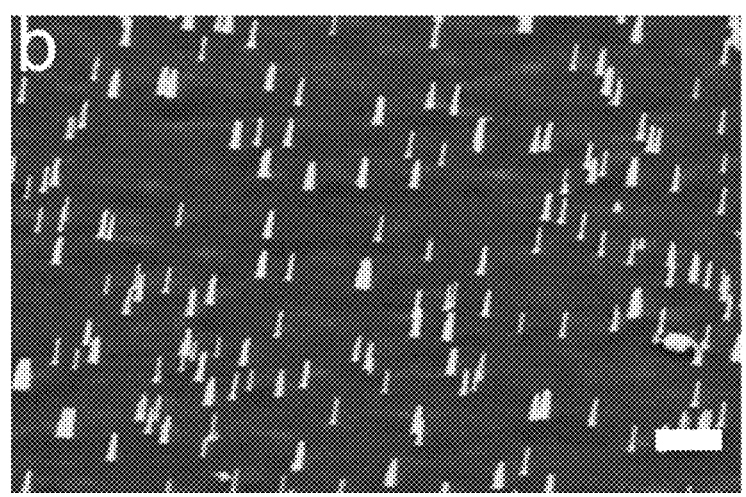
FIG. 3b is a scanning electron microscopy image of the non-functionalized nanoneedles used in an embodiment of the invention (scare bar, 20 µm).
Figure 3C:
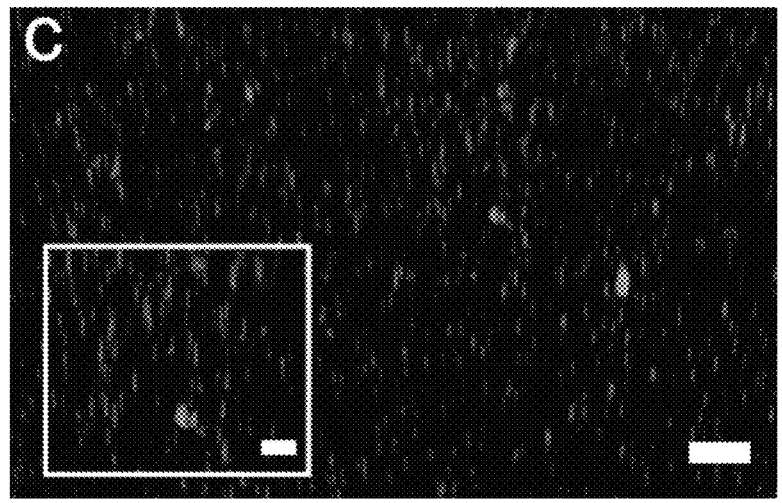
FIGS. 3c, 3d, 3e, and 3f are fluorescent confocal images of functionalized nanoneedles used in an embodiment of the invention (scare bar: 20 µm, the enlarged image scare bar: 10 µm).
Figure 3D:
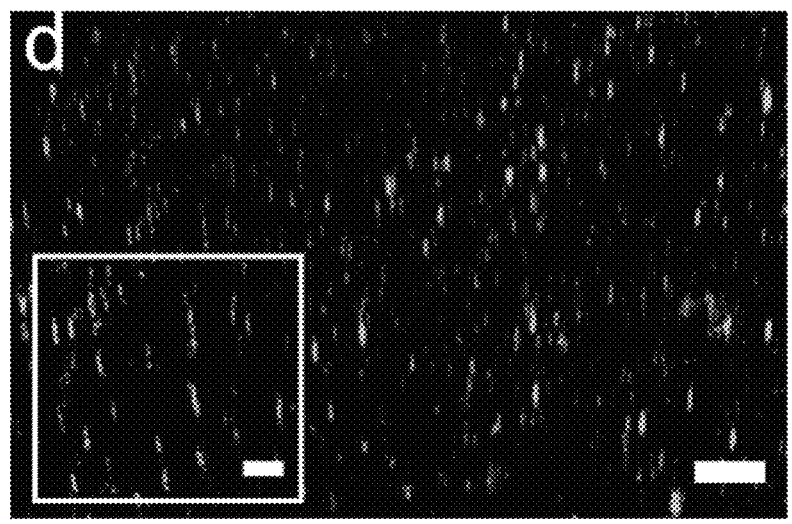
Figure 3E:
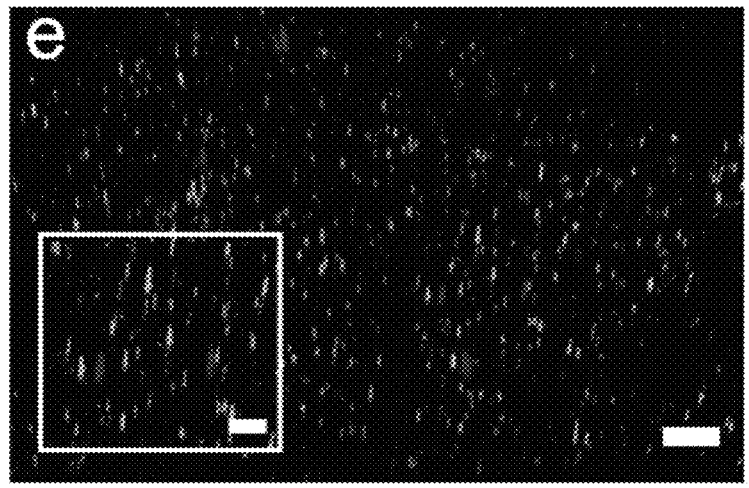
Figure 3F:
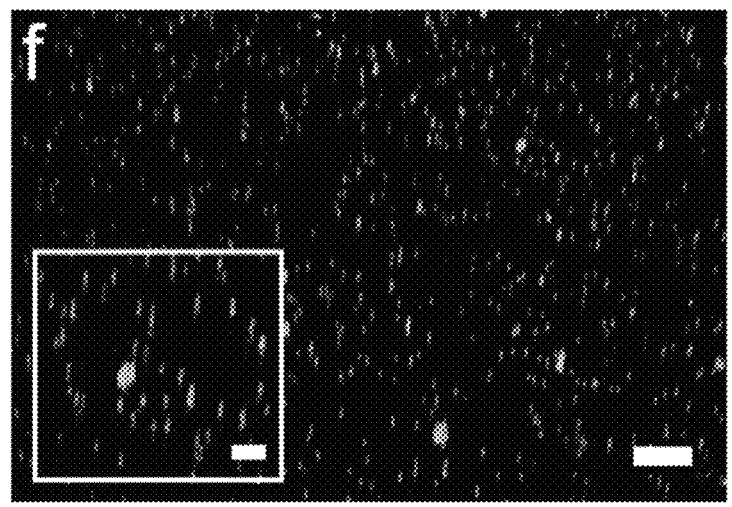
Figure 3G:
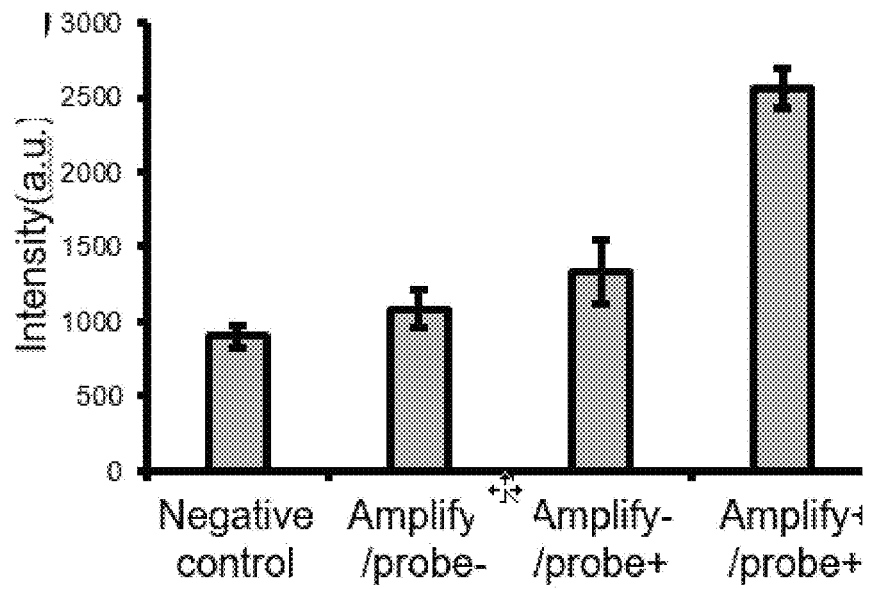
FIG. 3g shows the results obtained from the quantitative analysis of miRNA-34a positive signal under different conditions.

The method of the invention was conducted to determine a target RNA sequence, miR-34a, in living A549 cells. It is known that miR-34a plays an important role in p53 tumor suspensor network in A549 cells and present in at a relatively low expression level. With reference to FIG. 3a, the designed RNA probe was delivered into the cells by using an array of non-functionalized nanoneedles prepared in Example 2, under centrifugation condition. After that, the miR-34a sequences bound with the probes were extracted out using an array of functionalized nanoneedles. FIG. 3b-3f shows fluorescent spots observed under fluorescent microscope. These fluorescent spots were present on the surface of the nanoneedles. As shown in FIGS. 3c and 3d, when no probe has been delivered to the living cells, only few false positive signals can be detected. With reference to FIGS. 3c and 3e, in the absence of the hybridization step, there was no convincing florescent signal comparing with negative control group (no probes transfected). FIG. 3g shows the fluorescent intensity measured from the results obtained in FIGS. 3c to 3f.

Example 8

Interrogation of Live Cell miRNA Variation Under UV Treatment

Figure 4:
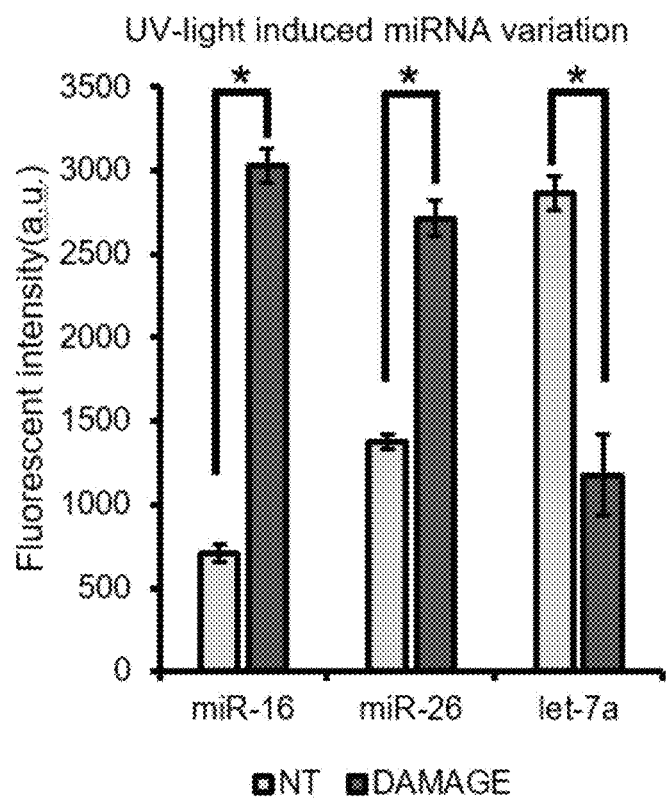
FIG. 4 shows the fluorescent intensity produced after each of target miR-16, miR-26 and let-7a sequences bind with their corresponding probe, with or without UV treatment, *$p<0.001$, by ANOVA analysis.

DNA damage is a common phenomenon happened in cells when they are exposed to intrinsic or extrinsic genotoxic stresses, like ultraviolet light (UV), ionizing radiation (IR), chemo- and radiotherapeutic agents. In order to determine the change of expression of nucleic acid within the intracellular environment, a further test was conducted in particular to demonstrate the miRNA variation in living cells under external DNA damage treatment. A549 cells were subject to UV treatment for real-time determination of the change in miRNA expression level in the early stage of DNA damage repair. As shown in the results of FIG. 4, Let-7a was down regulated in the first several minutes after UV treatment, while the expression level of miR-16 and miR-26 obviously increases. This test demonstrates that the method of the invention is capable of real-time monitoring the change of expression level of target nucleic acid while keeping the cells alive.

Example 9

Use of the Method and Kit in Identifying Cell Cycle Stage of the Cells

Figure 5A:
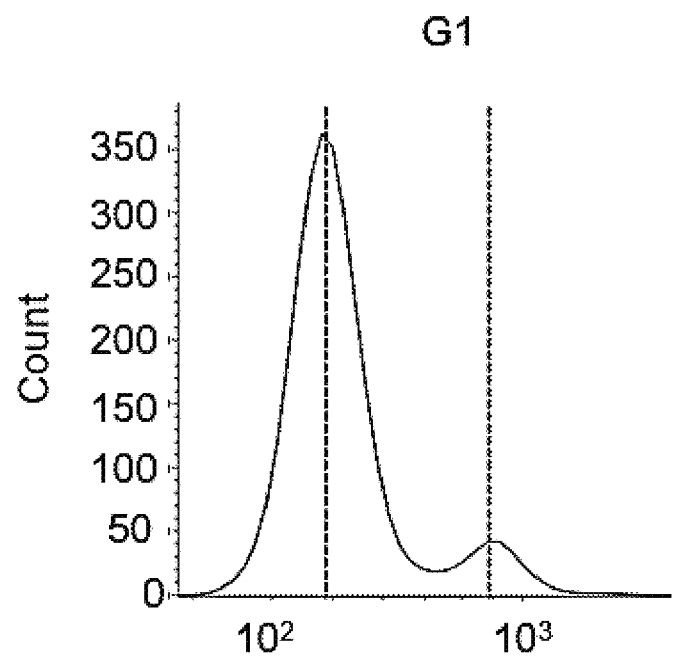
FIGS. 5A-C show the results obtained from PI staining flow cytometry analysis of cell cycle stage.
Figure 5B:
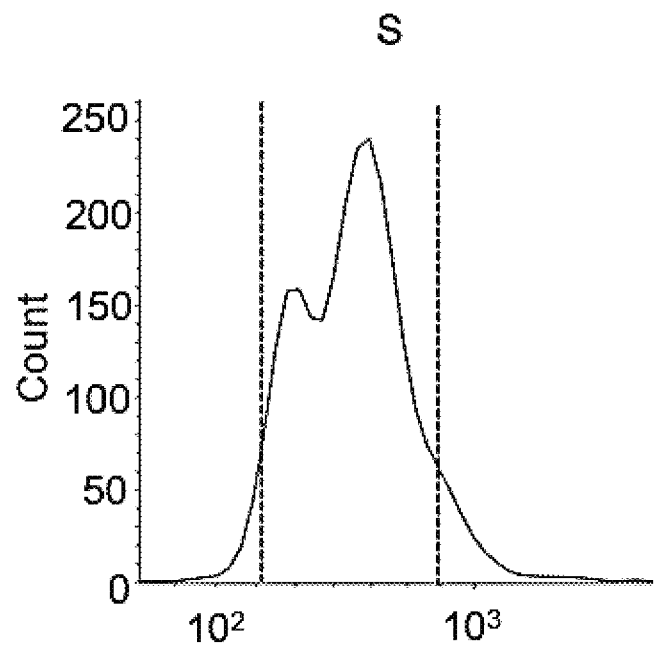
Figure 5C:
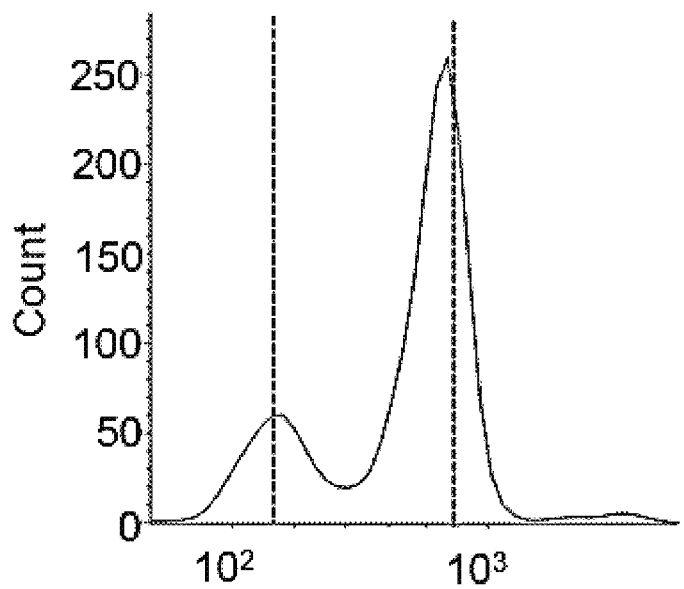
Figure 5D:
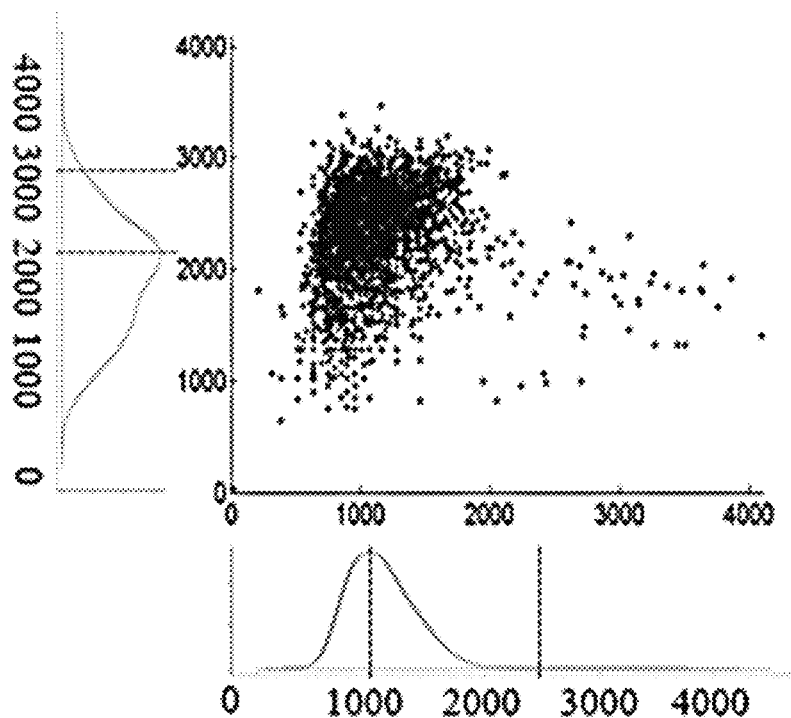
FIGS. 5D-F show scattering plots of multiplexed intracellular miRNA positive signal. X-panel, histogram of miRNA-21 signal and count (positive signal needle), Y-panel, histogram of miRNA-34 signal and count.
Figure 5E:
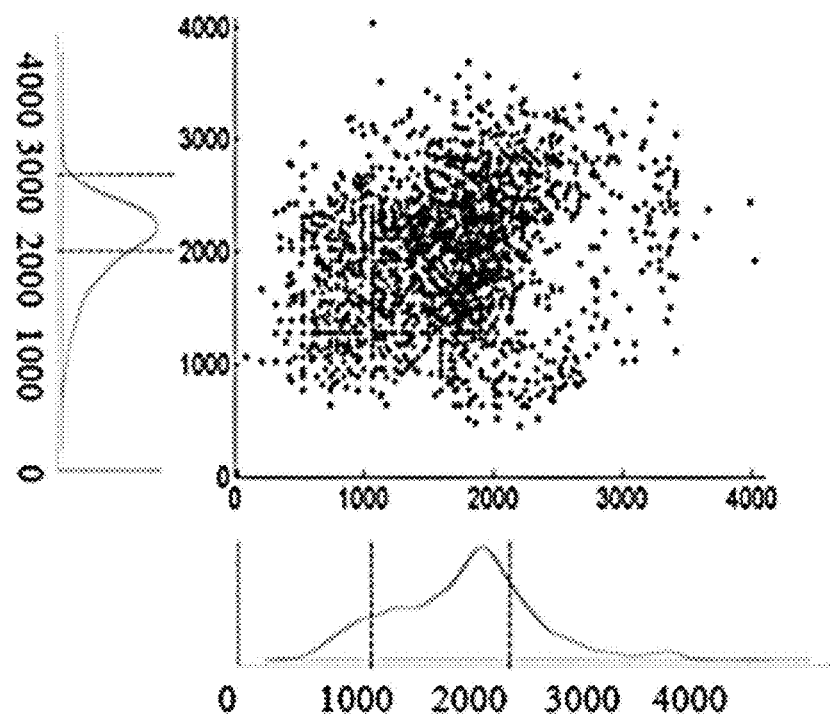
Figure 5F:
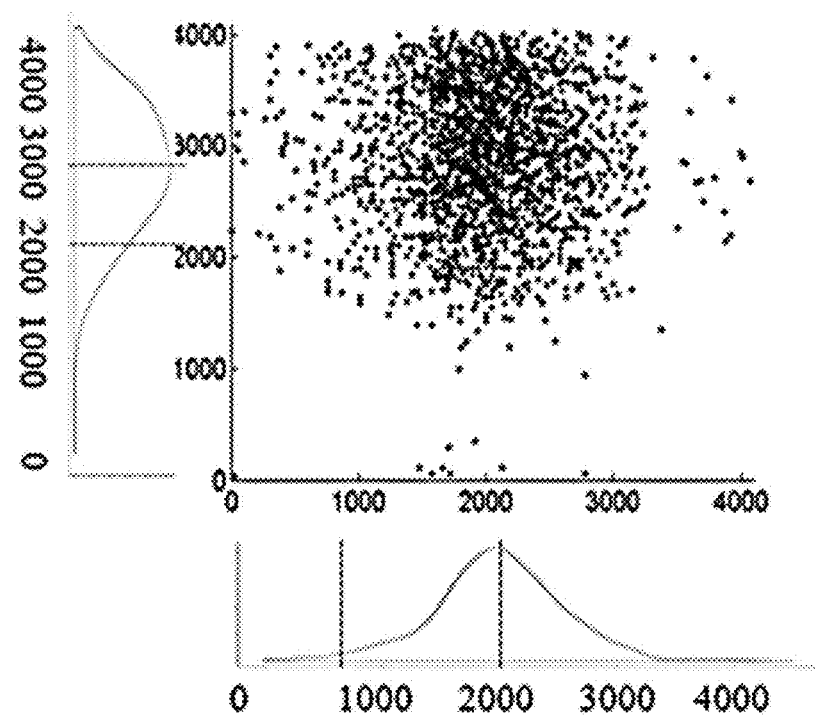
Figure 5G:
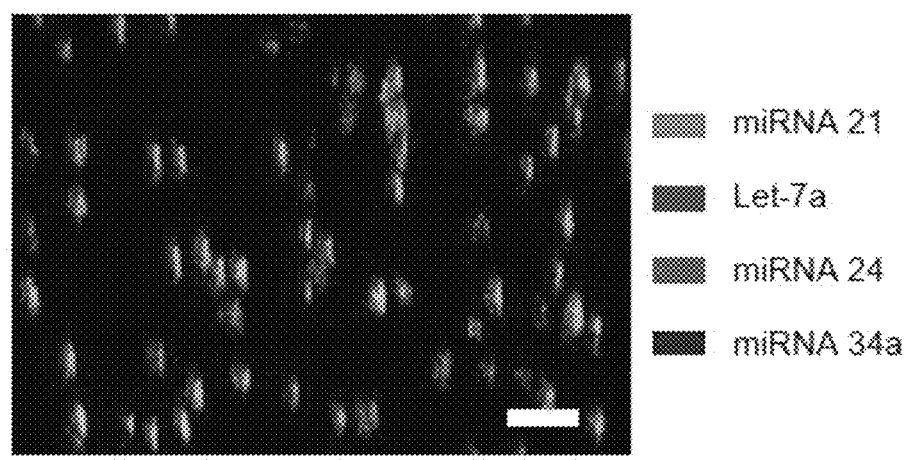
FIG. 5G is a 3D-reconstruction confocal fluorescent image of functionalized nanoneedle after extracting 4 target nucleic acids and amplification. Scare: 10 µm.
Figure 5H:
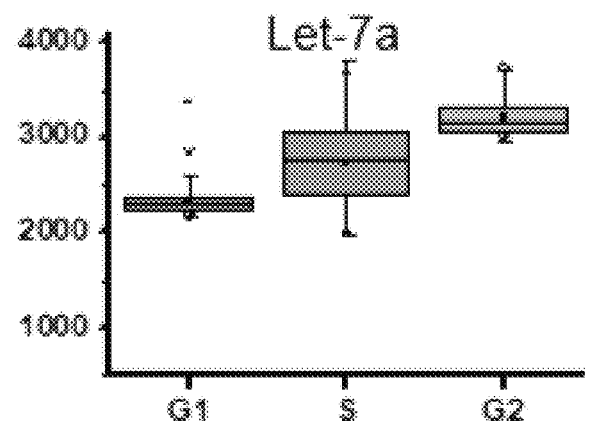
FIGS. 5H-K show box plots of the quantitative result of 4 miRNAs including let-7a (FIG. 5H), miR-21 (FIG. 5I), miR-24 (FIG. 5J) and miR-34a (FIG. 5K) at different cell cycle stage.
Figure 5I:
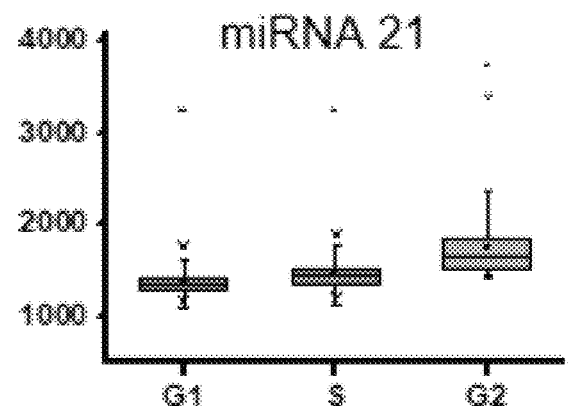
Figure 5J:
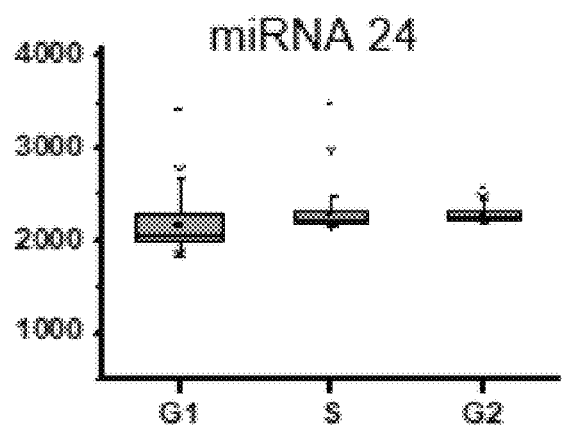
Figure 5K:
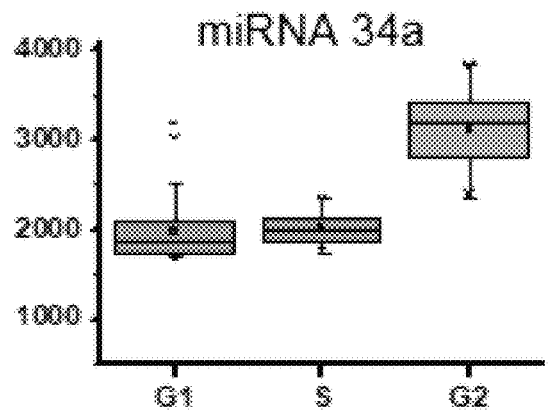
Figure 8:
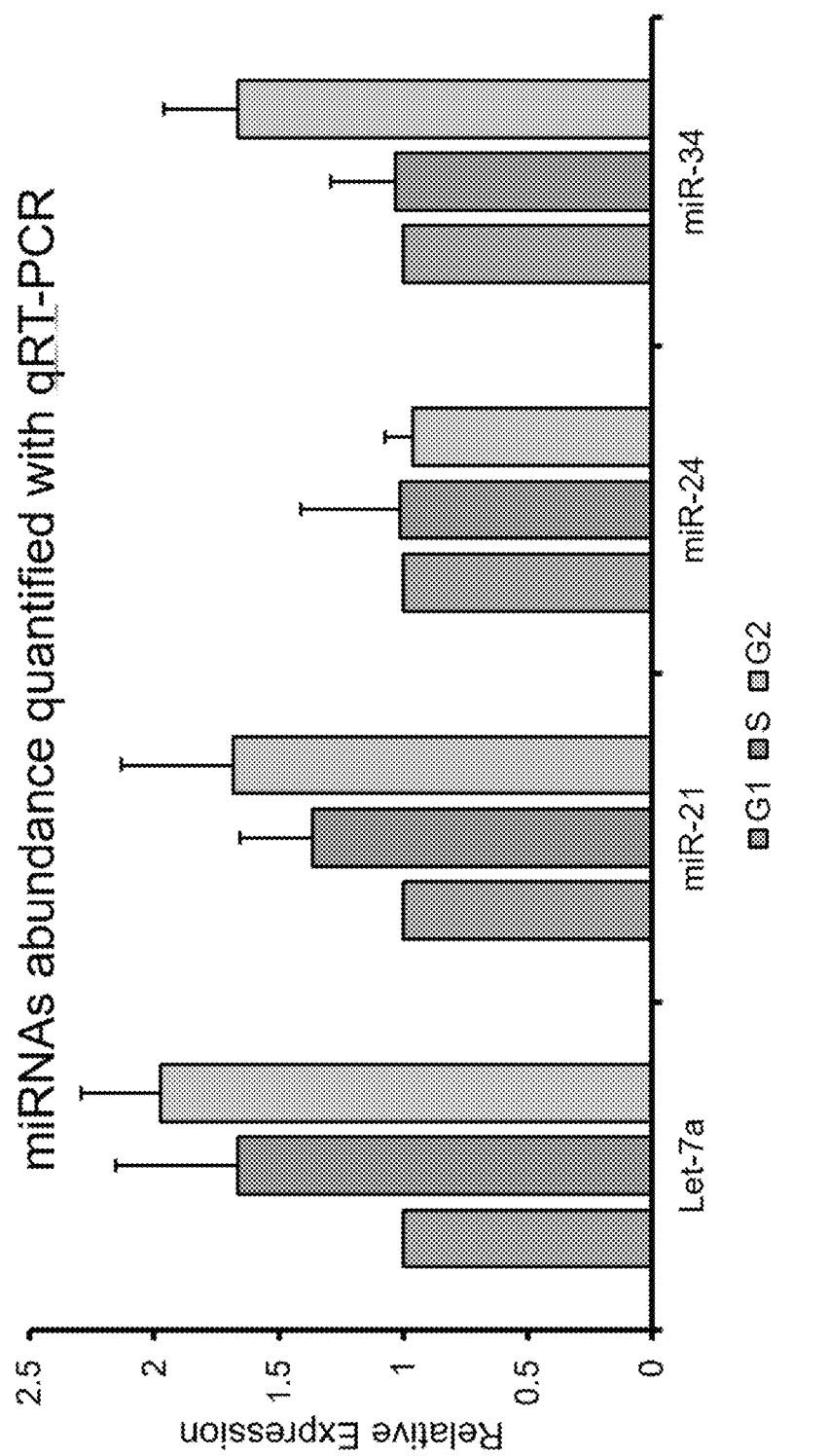
FIG. 8 shows relative expression of Let-7a, miR-21, miR-24, miR-34 at different cell cycle stage obtained from typical qRT-PCR method.
Figure 9A:
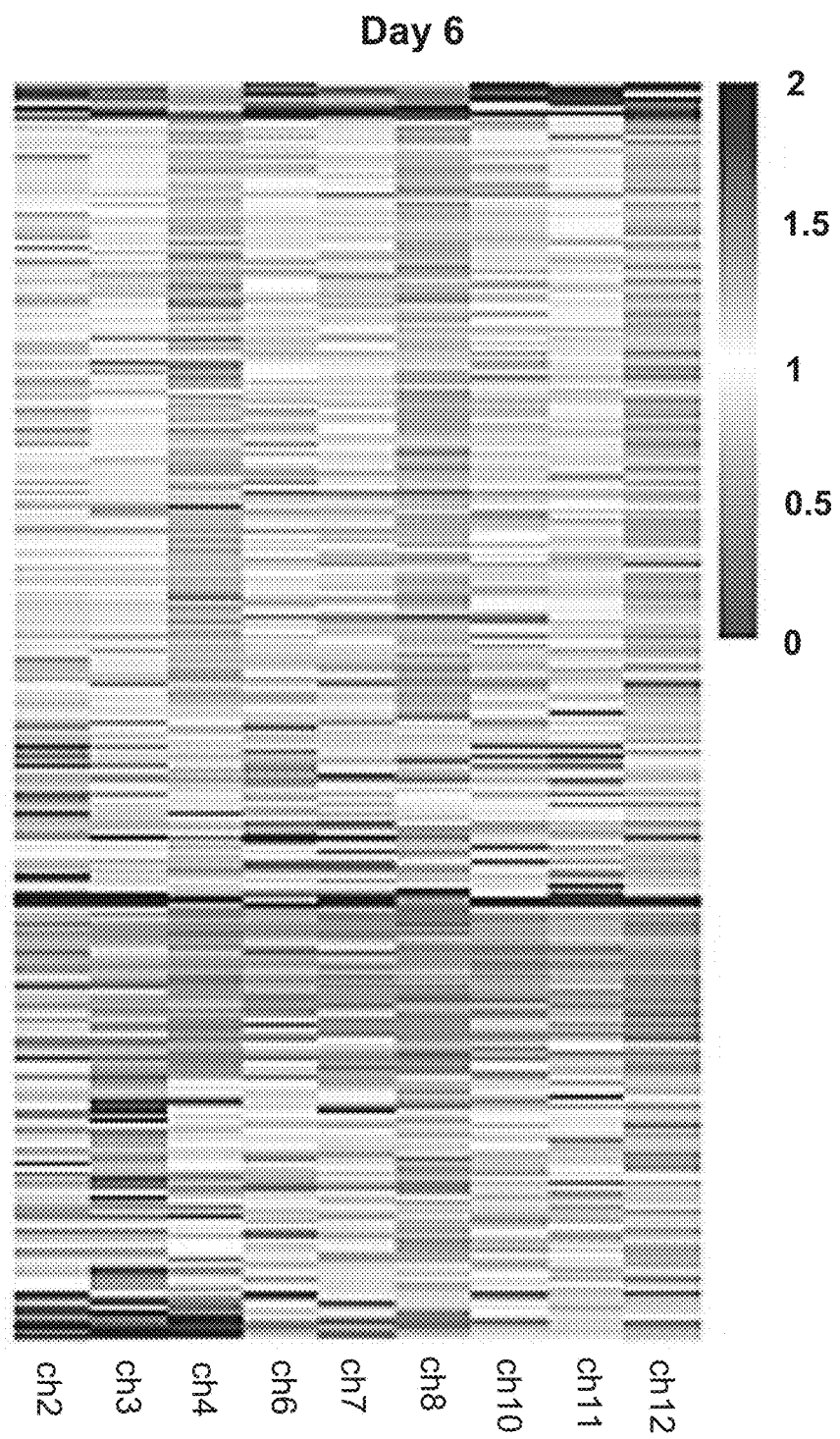
FIGS. 9a, 9b, 9c, and 9d show the results obtained from multiple miRNA expression pattern analysis during mESC differentiation.
Figure 9B:
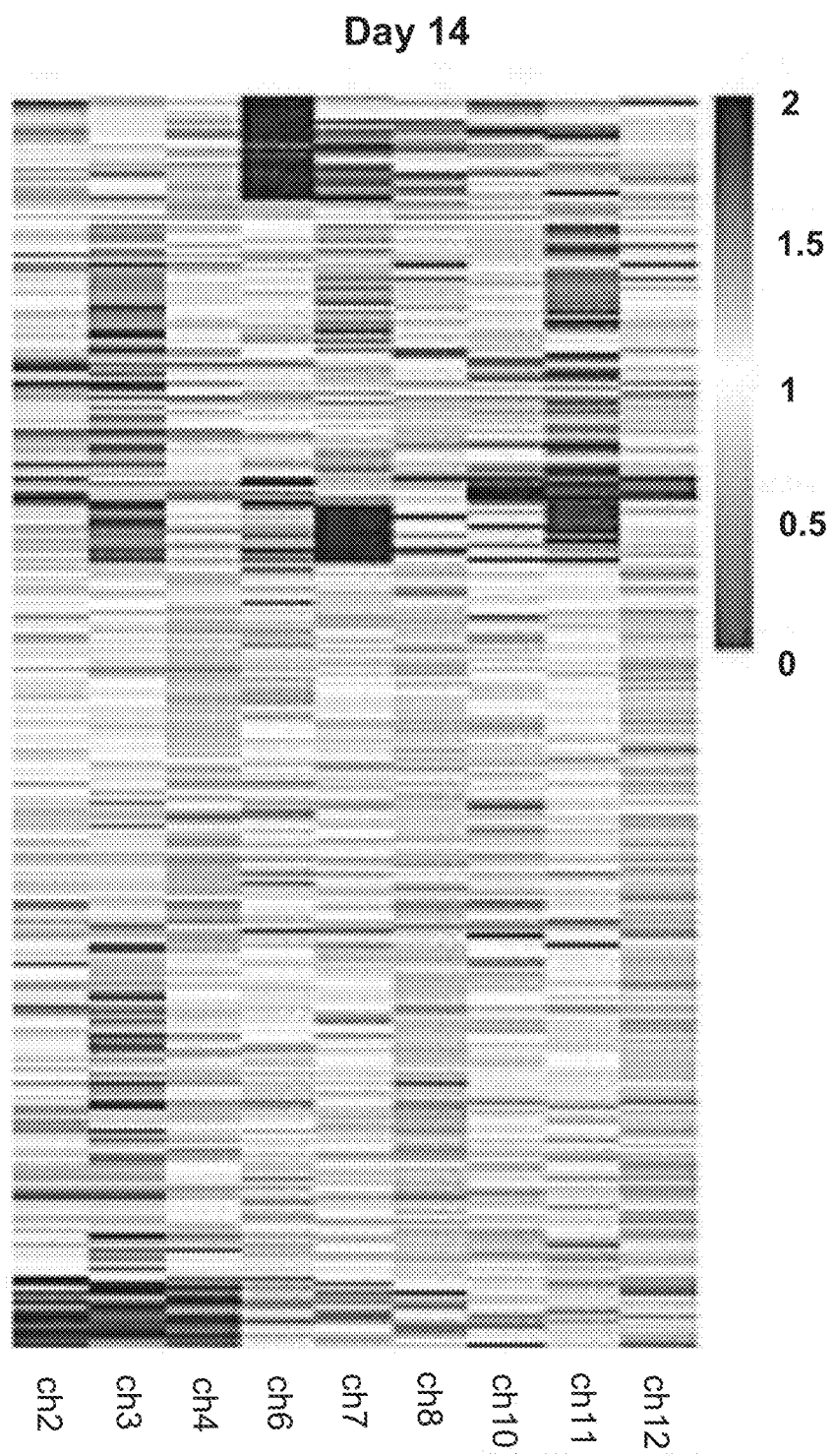
Figure 9C:
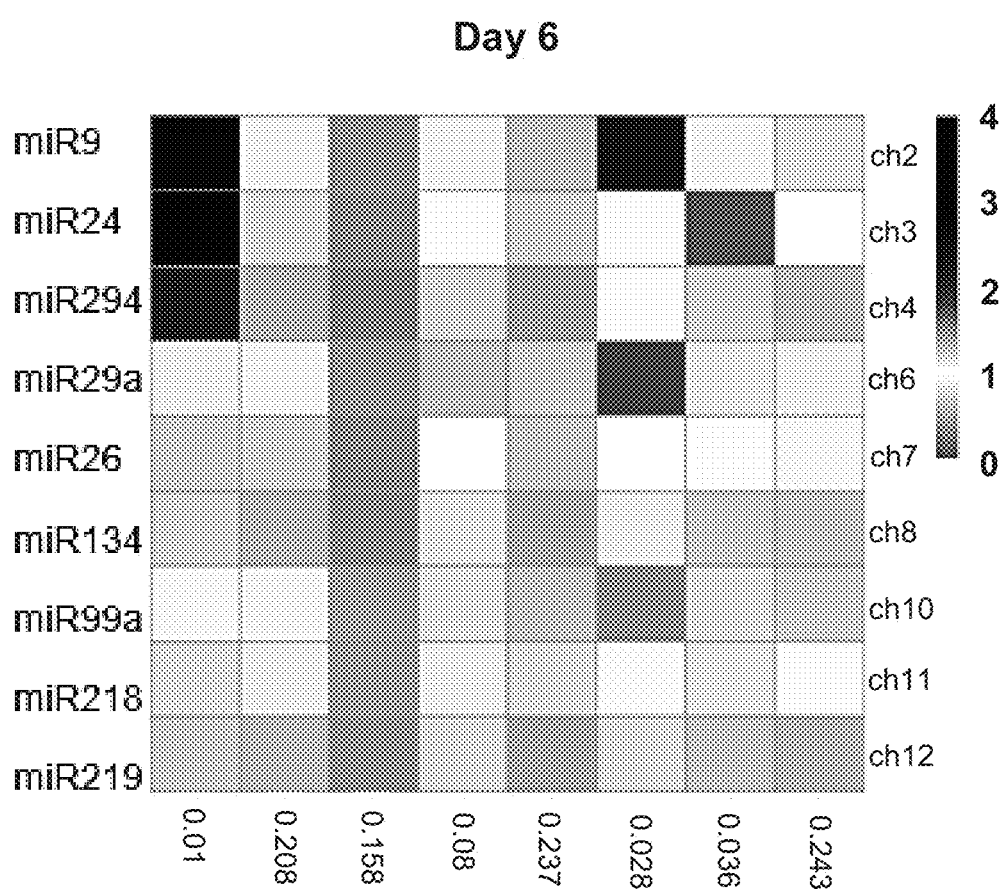
Figure 9D:
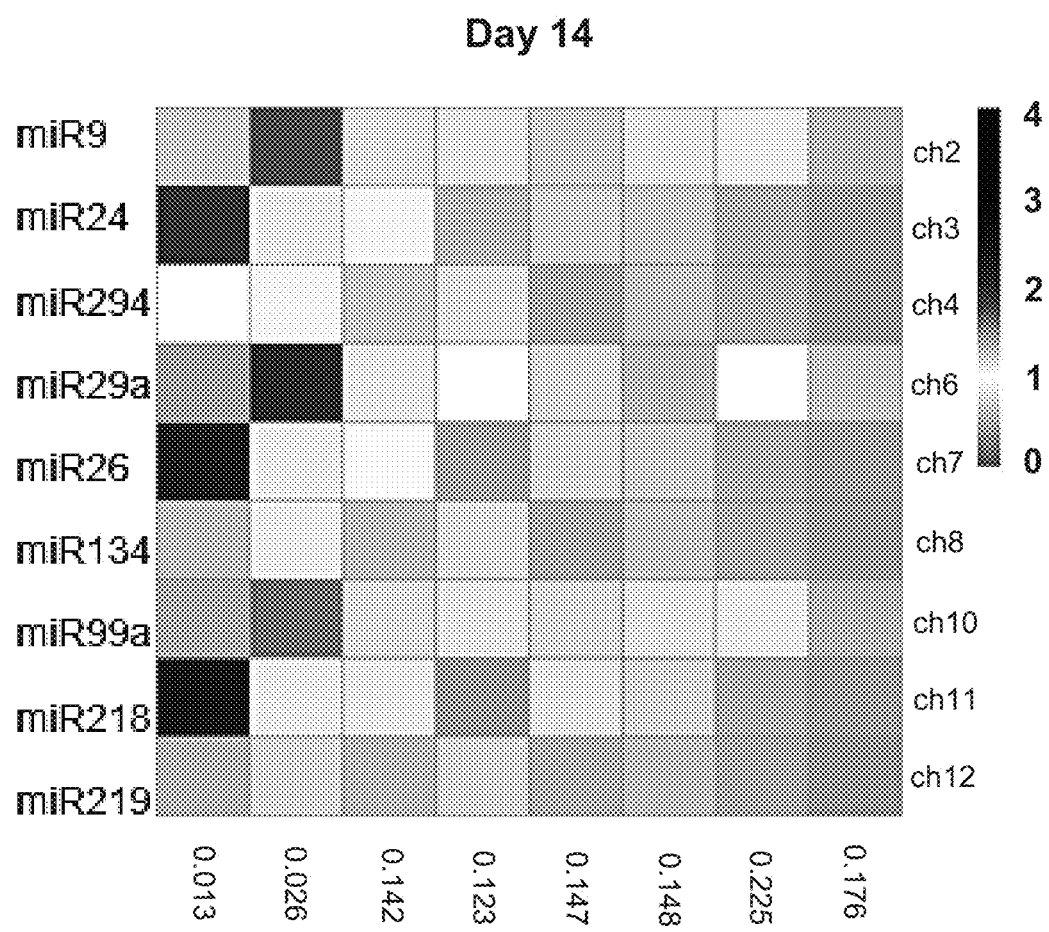

Cell cycle is a common phenomenon in cellular biology. Different miRNAs were reported involved in cell cycle regulation. The present method was applied to measure miRNA variation during the A549 cell cycle. 4 different florescent probes were used to bind with four different target nucleic acids. Referring to FIG. 5G, these 4 probes were delivered to the cells at the same time to collect the corresponding double-stranded RNA sequence respectively formed with single-stranded RNA sequence of miR-21, miR24, miR34a and let-7a. In particular, A549 cells were firstly synchronized at G1 stage. The 4 miRNAs were extracted at 01, S, G2 phase respectively. With reference to the quantitative results as shown in FIGS. 5A-F, the results show a good correlation with cell cycle phase. FIGS. 5H-K shows box plots of the quantitative result of 4 miRNAs including let-7a, miR-21, miR-24 and miR-34a at different cell cycle stage, A qRT-PCR using taqman miRNA kit was further conducted to confirm the results obtained by the present invention. The results as shown in FIG. 8 demonstrate that the results obtained by the method of the present invention are consistent with that obtained by typical qRT-PCR method.

Figure 6A:
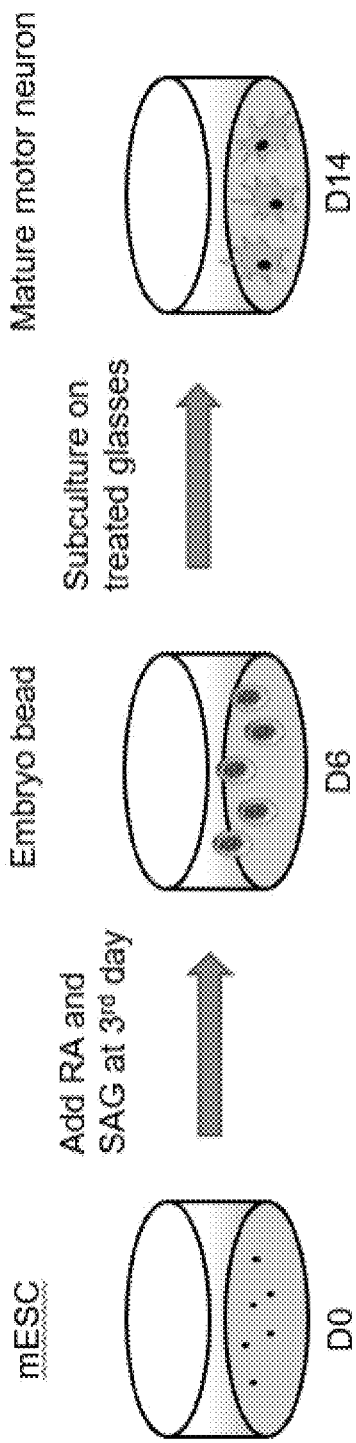
FIG. 6a is a schematic diagram showing the procedure of mESC induction.
Figure 6B:
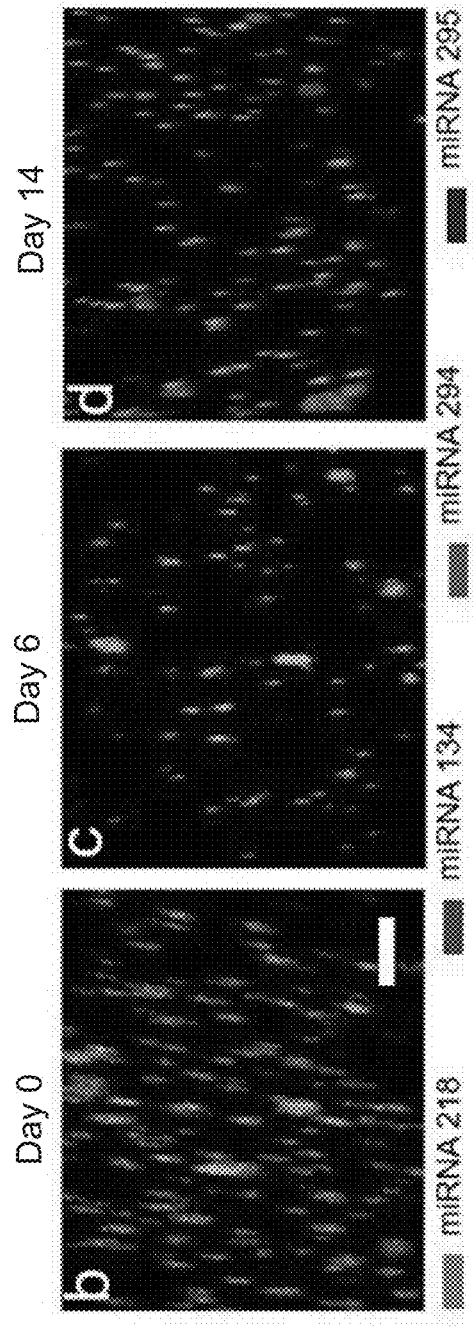
FIG. 6b are 3D-reconstruction confocal fluorescent images of functionalized nanoneedle after extracting nucleic acids and amplification from stem cells showing the presence or absence of miRNA 218, miRNA 134, miRNA 294 and miRNA 295 at Day 0, Day 6 and Day 14.
Figure 6C:
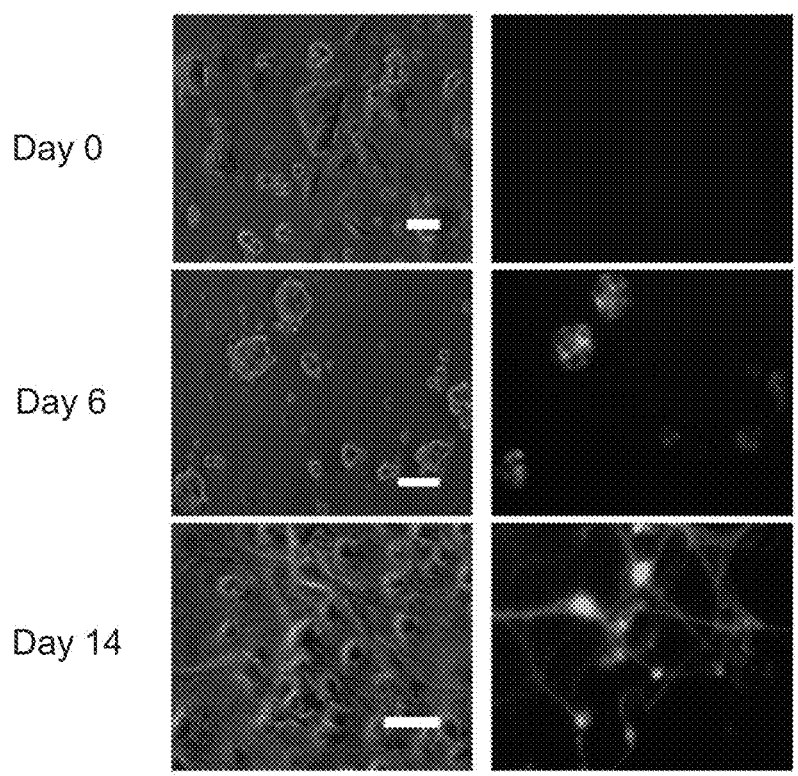
FIG. 6c is a blank field image (left panel) and fluorescent image (right panel) of stem cell morphology change at Day 0, Day 6 and Day 14. Scare bar: 50 µm.

In order to determine the heterogeneity variation during mESC differentiation, multiple miRNA expression pattern analysis must be utilized to represent different cell phenotype. The inventors applied the method of the present invention to analyze cellular heterogeneity change during stem cell differentiation. The stem cell was cultured in embryo stem cell (ESC) culture medium followed by differentiation medium and neural growth medium. Referring to FIG. 6a, in order to determine the cell heterogeneity at different differentiate stage, cells before induction (D0), and 6 days after induction (D6) and 14 days (D14) after induction were used. Two mESC specific miRNA sequences (miR294 and miR295) and two post differentiated specific miRNA sequences (miR134 and miR218) as expression markers were detected to track the differentiation stage as well as heterogeneity variation. With reference to FIG. 6b, the results are consistent that in the published papers. In particular, cells at day0 has a higher miR294, miR295 expression level while at day14 have a higher miR134 and miR218 expression level. However, with differentiation went on, the miRNA expression pattern spread into a more heterogeneous way. The cell morphology imaging also represents the same result, as shown in FIG. 6c.

To further investigate the miRNA expression pattern variation during mESC differentiation, a DNase was used. With the help of DNase, the inventors can erase all the DNA after the first amplification, and followed with another amplification with another set of initiator and hairpin sequence. This would help us extend our miRNA targets during one fish process. In particular, 9 target miRNA sequences were determined. The DNase was used after determination of each target sequence. Such that it enables the functionalized nanoneedles to be immersed in a mixture containing DNA sequences and initiating agent for the subsequent target sequence for determination. After collecting the data, cluster analysis was performed to interpret the data. Based on results as shown in FIGS. 9a to 9d, it is proved that the cells expressed different miRNA expression between Day 6 to Day 14.

The invention claimed is:

1. A method of determining the presence and/or amount of single-stranded RNA sequences, the method comprising steps of:
    a) delivering a plurality of probes into the cells, wherein:
        each of the plurality of probes is capable of binding with the single-stranded RNA sequences present in the cells to form a double-stranded sequence, each of the plurality of probes has an overhang sequence at an end, and each of the single-stranded RNA sequences has a known sequence and is composed of 15 to 30 nucleotides;
    b) inserting an array of functionalized nanoneedles into the cells to bind with the double-stranded sequence, wherein the functionalized nanoneedles comprise a RNA binding protein for binding with the double-stranded sequence, wherein the RNA binding protein does not bind with any double-stranded sequence having less than 15 nucleotides or more than 30 nucleotides or any single stranded sequence;
    c) removing the array of functionalized nanoneedles with the bound double-stranded sequence from the cells;
    d) hybridizing the bound double-stranded sequence starting at the overhang sequence with an initiating agent, a first DNA sequence and a second DNA sequence to produce a hybridized product, the initiating agent being a single-stranded nucleotide sequence, the first DNA sequence being partially complementary to the initiating agent and partially complementary to the second DNA sequence, and the second DNA sequence being partially complementary to the first DNA sequence and partially identical to the initiating agent for binding with another first DNA sequence to extend the bound double-stranded sequence, at least one of the first and second DNA sequence comprising a fluorophore molecule, the fluorophore molecule being 1,1'-bis(3-hydroxypropyl)-3,3,3',3'-tetramethylindocarbocyanine;
    e) washing the functionalized nanoneedles bound with the double-stranded sequence to remove impurities from the functionalized nanoneedles; and
    f) determining the presence and/or amount of the single-stranded RNA sequences in cells, which have a complementary sequence to the probes, based on signals of the fluorophore molecule,
    wherein the detection limit of the method is $10^{-16}$ M.

2. The method of claim 1, wherein each of the plurality of probes comprises a first region complementary to its target nucleic acid, and a second region for binding to the initiating agent.

3. The method of claim 2, wherein the second region of each of the plurality of probes has a length of between 5 bp to 20 bp.

4. The method of claim 1, wherein each of the first and second DNA sequence has a stem-loop structure, and the first and second DNA sequence hybridize with each other when one of them is open.

5. The method of claim 1, wherein the step b) is carried out by centrifugation to move the array of functionalized nanoneedles towards the cells for piercing the cells.

6. The method of claim 1, wherein the step d) comprises:
    immersing the functionalized nanoneedles with the bound double-stranded sequence into a first mixture containing the initiating agent,
    washing the functionalized nanoneedles and drying the washed functionalized nanoneedles; and
    immersing the functionalized nanoneedles with the bound double-stranded sequence into a second mixture containing the first and second DNA sequences to produce the hybridized product.

* * * * *